(12) United States Patent
Plahey et al.

(10) Patent No.: US 9,694,125 B2
(45) Date of Patent: Jul. 4, 2017

(54) MEDICAL FLUID CASSETTES AND RELATED SYSTEMS AND METHODS

(75) Inventors: Kulwinder S. Plahey, Martinez, CA (US); Robert Matthew Ohline, Redwood City, CA (US); Sean Farrell, Fresno, CA (US); Anthony Thomas Ortega, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 940 days.

(21) Appl. No.: 13/994,286

(22) PCT Filed: Dec. 16, 2011

(86) PCT No.: PCT/US2011/065415
§ 371 (c)(1),
(2), (4) Date: Oct. 8, 2013

(87) PCT Pub. No.: WO2012/087798
PCT Pub. Date: Jun. 28, 2012

(65) Prior Publication Data
US 2014/0018728 A1 Jan. 16, 2014

Related U.S. Application Data

(60) Provisional application No. 61/425,050, filed on Dec. 20, 2010.

(51) Int. Cl.
*A61M 1/16* (2006.01)
*A61M 1/28* (2006.01)
*F04B 43/02* (2006.01)

(52) U.S. Cl.
CPC ............... *A61M 1/16* (2013.01); *A61M 1/28* (2013.01); *A61M 2205/12* (2013.01); *A61M 2205/121* (2013.01); *F04B 43/02* (2013.01)

(58) Field of Classification Search
CPC ...... A61M 1/28; A61M 1/16; A61M 2205/12; A61M 2205/121; A61M 1/1055; A61M 5/31515; F04B 43/02
(Continued)

(56) References Cited

U.S. PATENT DOCUMENTS 329,773 A 11/1885 Perry
2,383,193 A 8/1945 Herbert
(Continued)

FOREIGN PATENT DOCUMENTS

DE 1816596 A1 7/1970
DE 2628238 1/1978
(Continued)

OTHER PUBLICATIONS

Gambro®, "DEHP-free cartridge blood sets," © Nov. 2004, Gambro, Inc., Lakewood, CO, 4 pp.
(Continued)

*Primary Examiner* — Theodore Stigell
*Assistant Examiner* — Benjamin Koo
(74) *Attorney, Agent, or Firm* — Fish & Richardson P.C.

(57) ABSTRACT

A medical fluid pumping system that includes a medical fluid pumping machine that includes an actuator and a medical fluid cassette that can be disposed within a cassette enclosure of the medical fluid pumping machine. A member is disposed within a fluid pump chamber of the medical fluid cassette and is magnetically attracted to the actuator such that the member and the actuator can be coupled together when the cassette is disposed within the cassette enclosure.

20 Claims, 24 Drawing Sheets

(58) Field of Classification Search
USPC .......................................................... 604/151
See application file for complete search history.

(56) References Cited

U.S. PATENT DOCUMENTS

| | | | |
|---|---|---|---|
| 2,886,281 A | 5/1959 | Canalizo | |
| 3,083,943 A | 4/1963 | Stewart, Jr. et al. | |
| 3,323,786 A | 6/1967 | Boschi | |
| 3,556,465 A | 1/1971 | Little | |
| 3,689,025 A | 9/1972 | Kiser et al. | |
| 3,880,053 A * | 4/1975 | Trechsel | F04B 15/00 92/103 R |
| 3,927,955 A | 12/1975 | Spinosa et al. | |
| 3,966,358 A | 6/1976 | Heimes et al. | |
| 3,985,135 A | 10/1976 | Carpenter et al. | |
| 4,026,669 A | 5/1977 | Leonard et al. | |
| 4,178,940 A | 12/1979 | Au | |
| 4,273,121 A | 6/1981 | Jassawalla | |
| 4,303,376 A | 12/1981 | Siekmann | |
| 4,333,452 A | 6/1982 | Au | |
| 4,370,983 A | 2/1983 | Lichtenstein | |
| 4,382,753 A | 5/1983 | Archibald | |
| 4,410,322 A | 10/1983 | Archibald | |
| 4,436,620 A | 3/1984 | Bellotti et al. | |
| 4,453,932 A | 6/1984 | Pastrone | |
| 4,479,762 A | 10/1984 | Bilstad et al. | |
| 4,558,715 A | 12/1985 | Walton et al. | |
| 4,569,378 A | 2/1986 | Bergandy | |
| 4,597,412 A | 7/1986 | Stark | |
| 4,623,328 A | 11/1986 | Hartranft | |
| 4,628,499 A | 12/1986 | Hammett | |
| 4,639,245 A | 1/1987 | Pastrone et al. | |
| 4,643,713 A | 2/1987 | Viitala | |
| 4,657,490 A | 4/1987 | Abbott | |
| 4,662,598 A | 5/1987 | Weingarten | |
| 4,662,906 A | 5/1987 | Matkovich et al. | |
| 4,676,467 A | 6/1987 | Palsulich | |
| 4,677,980 A * | 7/1987 | Reilly | A61M 5/007 128/DIG. 1 |
| 4,703,913 A | 11/1987 | Hunkapiller | |
| 4,705,259 A | 11/1987 | Dolhen et al. | |
| 4,710,166 A | 12/1987 | Thompson et al. | |
| 4,778,451 A | 10/1988 | Kamen | |
| 4,808,161 A | 2/1989 | Kamen | |
| 4,826,482 A | 5/1989 | Kamen | |
| 4,840,542 A | 6/1989 | Abbott | |
| 4,842,584 A | 6/1989 | Pastrone | |
| 4,846,636 A | 7/1989 | Danby et al. | |
| 4,902,282 A | 2/1990 | Bellotti et al. | |
| 4,906,260 A | 3/1990 | Emheiser et al. | |
| 4,927,411 A | 5/1990 | Pastrone et al. | |
| 4,950,134 A | 8/1990 | Bailey et al. | |
| 4,976,162 A | 12/1990 | Kamen | |
| 4,997,464 A | 3/1991 | Kopf | |
| 5,002,471 A | 3/1991 | Perlov | |
| 5,036,886 A | 8/1991 | Olsen et al. | |
| 5,061,236 A | 10/1991 | Sutherland et al. | |
| 5,088,515 A | 2/1992 | Kamen | |
| 5,098,262 A | 3/1992 | Wecker et al. | |
| 5,100,380 A | 3/1992 | Epstein | |
| 5,100,699 A | 3/1992 | Roeser | |
| 5,116,021 A | 5/1992 | Faust et al. | |
| 5,116,316 A | 5/1992 | Sertic et al. | |
| 5,146,713 A | 9/1992 | Grafius | |
| 5,151,019 A | 9/1992 | Danby et al. | |
| 5,167,837 A | 12/1992 | Snodgrass et al. | |
| 5,171,029 A | 12/1992 | Maxwell et al. | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,247,434 A | 9/1993 | Peterson et al. | |
| 5,252,044 A | 10/1993 | Raines et al. | |
| 5,279,556 A | 1/1994 | Goi et al. | |
| 5,302,093 A | 4/1994 | Owens et al. | |
| 5,324,422 A | 6/1994 | Colleran et al. | |
| 5,330,425 A | 7/1994 | Utterberg | |
| 5,350,357 A | 9/1994 | Kamen et al. | |
| D351,470 S | 10/1994 | Scherer et al. | |
| 5,353,837 A | 10/1994 | Faust | |
| 5,378,126 A | 1/1995 | Abrahamson et al. | |
| 5,395,351 A | 3/1995 | Munsch | |
| 5,415,528 A | 5/1995 | Ogden et al. | |
| 5,421,208 A | 6/1995 | Packard et al. | |
| 5,421,823 A | 6/1995 | Kamen et al. | |
| 5,427,509 A | 6/1995 | Chapman et al. | |
| 5,431,626 A | 7/1995 | Bryant et al. | |
| 5,431,627 A | 7/1995 | Pastrone et al. | |
| 5,431,634 A | 7/1995 | Brown | |
| 5,438,510 A | 8/1995 | Bryant et al. | |
| 5,441,636 A | 8/1995 | Chevallet et al. | |
| 5,445,506 A | 8/1995 | Afflerbaugh et al. | |
| 5,447,286 A | 9/1995 | Kamen et al. | |
| 5,462,416 A | 10/1995 | Dennehey et al. | |
| 5,462,417 A | 10/1995 | Chapman | |
| 5,474,683 A | 12/1995 | Bryant et al. | |
| 5,478,211 A | 12/1995 | Dominiak et al. | |
| 5,480,294 A | 1/1996 | Di Perna et al. | |
| 5,482,438 A | 1/1996 | Anderson et al. | |
| 5,482,440 A | 1/1996 | Dennehey et al. | |
| 5,482,446 A | 1/1996 | Williamson et al. | |
| 5,484,239 A | 1/1996 | Chapman et al. | |
| 5,486,286 A | 1/1996 | Peterson et al. | |
| 5,514,069 A | 5/1996 | Brown et al. | |
| 5,538,405 A | 7/1996 | Patno et al. | |
| 5,540,568 A | 7/1996 | Rosen et al. | |
| 5,547,453 A | 8/1996 | Di Perna | |
| 5,551,850 A | 9/1996 | Williamson et al. | |
| 5,551,941 A | 9/1996 | Howell | |
| 5,551,942 A | 9/1996 | Brown et al. | |
| 5,554,013 A | 9/1996 | Owens et al. | |
| 5,570,716 A | 11/1996 | Kamen et al. | |
| 5,578,070 A | 11/1996 | Utterberg | |
| 5,609,572 A | 3/1997 | Lang | |
| 5,614,677 A | 3/1997 | Wamsiedler et al. | |
| 5,628,908 A | 5/1997 | Kamen et al. | |
| 5,630,710 A | 5/1997 | Tune et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,643,205 A | 7/1997 | Utterberg | |
| 5,658,133 A | 8/1997 | Anderson et al. | |
| 5,690,602 A | 11/1997 | Brown et al. | |
| D390,654 S | 2/1998 | Alsberg et al. | |
| 5,713,865 A | 2/1998 | Manning et al. | |
| 5,713,888 A | 2/1998 | Neuenfeldt et al. | |
| 5,741,125 A | 4/1998 | Neftel et al. | |
| 5,746,708 A | 5/1998 | Giesler et al. | |
| 5,755,683 A | 5/1998 | Houle et al. | |
| 5,764,034 A | 6/1998 | Bowman et al. | |
| 5,769,387 A | 6/1998 | Perez | |
| 5,771,914 A | 6/1998 | Ling et al. | |
| 5,772,635 A | 6/1998 | Dastur et al. | |
| 5,772,637 A | 6/1998 | Heinzmann et al. | |
| 5,775,371 A | 7/1998 | Pan et al. | |
| 5,782,575 A | 7/1998 | Vincent et al. | |
| 5,782,805 A | 7/1998 | Meinzer et al. | |
| 5,799,207 A | 8/1998 | Wang et al. | |
| 5,816,779 A | 10/1998 | Lawless et al. | |
| 5,840,151 A | 11/1998 | Munsch | |
| 5,842,841 A | 12/1998 | Danby et al. | |
| 5,843,035 A | 12/1998 | Bowman et al. | |
| 5,868,696 A | 2/1999 | Giesler et al. | |
| 5,873,853 A | 2/1999 | Keilman et al. | |
| 5,906,598 A | 5/1999 | Giesler et al. | |
| 5,921,951 A | 7/1999 | Morris | |
| 5,925,011 A | 7/1999 | Faict et al. | |
| 5,935,099 A | 8/1999 | Peterson et al. | |
| 5,938,634 A | 8/1999 | Packard | |
| 5,989,423 A | 11/1999 | Kamen et al. | |
| 5,993,174 A | 11/1999 | Konishi | |
| 5,996,634 A | 12/1999 | Dennehey et al. | |
| 6,013,057 A | 1/2000 | Danby et al. | |

(56) References Cited

U.S. PATENT DOCUMENTS

| | | |
|---|---|---|
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,099,492 A | 8/2000 | Le Boeuf |
| 6,110,410 A | 8/2000 | Owens et al. |
| 6,118,207 A | 9/2000 | Ormerod et al. |
| 6,129,517 A | 10/2000 | Danby et al. |
| 6,136,565 A | 10/2000 | Best et al. |
| 6,154,605 A | 11/2000 | Aonuma |
| 6,164,621 A | 12/2000 | Bouchard et al. |
| 6,165,154 A | 12/2000 | Gray et al. |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,208,107 B1 | 3/2001 | Maske et al. |
| 6,220,295 B1 | 4/2001 | Bouchard et al. |
| 6,223,130 B1 | 4/2001 | Gray et al. |
| 6,227,807 B1 | 5/2001 | Chase |
| 6,228,047 B1 | 5/2001 | Dadson |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Doenig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,211,560 B2 | 5/2007 | Looker et |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,267,661 B2 | 9/2007 | Susi |
| 7,306,578 B2 | 12/2007 | Gray et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |

(56) References Cited

U.S. PATENT DOCUMENTS

| | | |
|---|---|---|
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,789,849 B2 | 9/2010 | Busby et al. |
| 7,815,595 B2 | 10/2010 | Busby et al. |
| 8,366,921 B2 | 2/2013 | Beden et al. |
| 2001/0034502 A1 | 10/2001 | Moberg et al. |
| 2001/0037763 A1 | 11/2001 | Deguchi et al. |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0141529 A1 | 10/2002 | Olsher et al. |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0079826 A1 | 4/2006 | Beden et al. |
| 2006/0195064 A1 | 8/2006 | Plahey et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2007/0278155 A1* | 12/2007 | Lo .................... A61M 1/16 210/646 |
| 2008/0033346 A1 | 2/2008 | Childers et al. |
| 2008/0077068 A1 | 3/2008 | Orr |
| 2008/0093246 A1* | 4/2008 | Duchamp .............. B65D 85/38 206/438 |
| 2008/0208103 A1 | 8/2008 | Demers et al. |
| 2009/0004033 A1 | 1/2009 | Demers et al. |
| 2010/0241062 A1 | 9/2010 | Morris et al. |
| 2010/0274168 A1* | 10/2010 | Gronau ................ A61M 1/30 604/5.04 |
| 2011/0092895 A1 | 4/2011 | Yardimci et al. |
| 2011/0137237 A1 | 6/2011 | Prisco et al. |
| 2012/0051956 A1* | 3/2012 | Grip .................... A61M 5/1413 417/413.1 |
| 2012/0065581 A1 | 3/2012 | Childers et al. |

FOREIGN PATENT DOCUMENTS

| | | |
|---|---|---|
| DE | 2827648 | 1/1979 |
| DE | 4006785 | 9/1990 |
| DE | 4118628 A1 | 12/1992 |
| DE | 4336336 | 5/1994 |
| DE | 19837667 | 3/2000 |
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 0410125 B1 | 8/1993 |
| EP | 0728509 | 8/1996 |
| EP | 0848193 | 6/1998 |
| EP | 0856321 | 8/1998 |
| EP | 0947814 | 10/1999 |
| EP | 0956876 | 11/1999 |
| EP | 1529545 | 5/2005 |
| GB | 1483702 | 8/1977 |
| GB | 2101232 A | 1/1983 |
| GB | 2331796 | 6/1999 |
| JP | 0396850 A | 4/1991 |
| JP | 04191755 | 7/1992 |
| JP | 06154314 | 6/1994 |
| JP | 06002650 | 11/1994 |
| JP | 08028722 | 2/1996 |
| JP | 11347115 | 12/1999 |
| JP | 2000070358 | 3/2000 |
| JP | 2000346214 | 12/2000 |
| WO | 8402473 | 7/1984 |
| WO | 8601115 | 2/1986 |
| WO | 9420155 | 9/1994 |
| WO | 9625064 | 8/1996 |
| WO | 9716214 | 5/1997 |
| WO | 9737703 | 10/1997 |
| WO | 9822165 | 5/1998 |
| WO | 0023140 | 4/2000 |
| WO | 0033898 | 6/2000 |
| WO | 0117605 | 3/2001 |
| WO | 0225146 | 3/2002 |
| WO | 0225225 | 3/2002 |
| WO | 03072161 A2 | 9/2003 |
| WO | 2009071069 | 6/2009 |

OTHER PUBLICATIONS

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Glenn Avolio, "Principles of Rotary Optical Encoders," Sensors Journal of Machine Perception, vol. 10, No. 4, pp. 10-18, 1993.

Manns, Markus et al., "The acu-men: A new device for continuous renal replacement therapy in acute renal failure," Kidney International, vol. 54, pp. 268-274, 1998.

Liberty Cycler Operator's Manual, 2003-2004.

Newton IQ Cycler Operator Manual, Part No. 470203 Rev. F, 2000-2006.

Operator's Instructions, Fresenius 90/2 Peritoneal Therapy Cycler, Part No. 470016, Rev. B, 1991.

Operator's Manual, Serena, Program Version 3.xx—English, 2002.

Sleep Safe Operating Instructions, Software Version 0.9, Part No. 677 801 1; Aug. 2000.

Sleep Safe Technical Manual, Part No. 677 807 1; Aug. 2000.

(56) References Cited

OTHER PUBLICATIONS

Notification of Transmittal of the International Search Report and the Written Opinion of the International Searching Authority for corresponding PCT Application No. PCT/US2011/065415, mailed Jul. 12, 2013, 15 pages.
Bolegoh, Gordon, "Pumps: Reference Guide", p. 24, 3rd edition, 2001.
Ronco et al., "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).

\* cited by examiner

MEDICAL FLUID CASSETTES AND RELATED SYSTEMS AND METHODS

CROSS-REFERENCE TO RELATED APPLICATIONS

This application is a 371 of PCT/US2011/065415, filed on Dec. 16, 2011, which claims the benefit of U.S. Provisional Application No. 61/425,050, filed on Dec. 20, 2010, which is incorporated by reference herein.

TECHNICAL FIELD

This disclosure relates to medical fluid cassettes and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine defining a cassette enclosure and including an actuator. The system also includes a medical fluid cassette configured to be disposed within the cassette enclosure of the medical fluid pumping machine. The medical fluid cassette includes a base and a membrane attached to the base. The membrane and a region of the base cooperate to define a fluid pump chamber, and the cassette is positionable within the cassette enclosure of the medical fluid pumping machine so that the actuator is substantially aligned with the fluid pump chamber. A member is disposed within the fluid pump chamber and is magnetically attracted to the actuator such that the member and the actuator can be coupled together with a portion of the membrane positioned between the actuator and the member when the cassette is disposed within the cassette enclosure.

In another aspect of the invention, a medical fluid cassette includes a base and a membrane attached to the base. The membrane and a region of the base cooperate to define a fluid pump chamber. The medical fluid cassette also includes a member disposed within the fluid pump chamber. The member is shaped to substantially conform to the region of the base that defines the fluid pump chamber, and the member is magnetically attracted to an actuator of a medical fluid pumping machine when the medical fluid cassette is disposed within a cassette enclosure of the medical fluid pumping machine.

In an additional aspect of the invention, a medical fluid pumping machine, includes a base and a door secured to the base. The base and the door together define a cassette enclosure when the door is closed. At least one actuator is at least partially disposed in a port defined by the base. The actuator is magnetically attracted to a member disposed within a fluid pump chamber of a medical fluid cassette when the medical fluid cassette is disposed within the cassette enclosure of the medical fluid pumping machine.

In a further aspect of the invention, a medical fluid delivery method includes magnetically coupling an actuator of a medical fluid pumping machine to a member disposed in a fluid pump chamber of a medical fluid cassette and, while the actuator and the member are coupled to one another, retracting the actuator and the member to increase the volume of the fluid pump chamber and draw fluid into the fluid pump chamber of the medical fluid cassette.

In another aspect of the invention, a medical fluid delivery method includes drawing medical fluid into a fluid pump chamber defined between a membrane and a rigid base of a medical fluid cassette by magnetically attracting a member disposed in the fluid pump chamber to an actuator and retracting the actuator such that a portion of the membrane disposed between the member and the actuator is moved outwardly, thereby increasing the volume of the pump chamber.

In an additional aspect of the invention, a medical fluid pumping system includes a medical fluid pumping machine defining a cassette enclosure and including a piston with a magnetic piston head. The system also includes a medical fluid cassette configured to be disposed within the cassette enclosure of the medical fluid pumping machine. The medical fluid cassette includes a base and a membrane attached to the base. The membrane and a region of the base cooperate to define a fluid pump chamber, and the cassette is positionable within the cassette enclosure of the medical fluid pumping machine so that the piston head is substantially aligned with the fluid pump chamber. The membrane is magnetically attracted to the piston head such that the membrane and the piston can be coupled together when the cassette is disposed within the cassette enclosure.

In a further aspect of the invention, a medical fluid cassette includes a base and a membrane attached to the base. The membrane and a region of the base cooperate to define a fluid pump chamber, and the membrane is magnetically attracted to a piston head of a medical fluid pumping machine when the medical fluid cassette is disposed within a cassette enclosure of the medical fluid pumping machine.

In another aspect of the invention, a medical fluid pumping machine includes a base and a door secured to the base.

The base and the door together define a cassette enclosure when the door is closed. A piston is at least partially disposed in a port defined by the base, and the piston includes a piston head that is magnetically attracted to a portion of a membrane overlying a fluid pump chamber of a medical fluid cassette when the medical fluid cassette is disposed within the cassette enclosure of the medical fluid pumping machine.

In an additional aspect of the invention, a medical fluid delivery method includes magnetically coupling a piston head of a medical fluid pumping machine to a portion of a membrane overlying and at least partially defining a fluid pump chamber of a medical fluid cassette, and, while the piston head and the membrane are coupled to one another, retracting the piston head and the membrane to increase the volume of the fluid pump chamber and draw fluid into the fluid pump chamber of the medical fluid cassette.

Implementations can include one or more of the following features.

In some implementations, the member is shaped to substantially conform to a recess in the region of the base that cooperates with the membrane to form the fluid pump chamber.

In some implementations, the member and the recess in the region of the base that cooperates with the membrane to form the fluid pump chamber are substantially dome-shaped.

In some implementations, the actuator includes one or more magnets, and the member includes a magnetic material that is attracted to the magnets.

In some implementations, the member includes a magnetic plate that is secured to a non-magnetic material.

In some implementations, the magnetic plate is surrounded by the non-magnetic material.

In some implementations, the non-magnetic material is a polymeric material (e.g., polyoxymethylene).

In some implementations, the magnetic plate includes a ferromagnetic material (e.g., steel).

In some implementations, the actuator includes a magnet plate that defines multiple recesses and multiple magnets disposed in the recesses.

In some implementations, a magnetic force of the actuator can be altered by altering the number of magnets disposed within the recesses of the magnet plate.

In some implementations, a magnetic field surrounding the actuator is no greater than about 10 Gauss (e.g., no greater than about 5 Gauss) at a distance of about 1.5 inches from the magnet plate.

In some implementations, the magnets are arranged in the recesses such that at least some adjacent magnets have opposite polarities.

In some implementations, at least some of the magnets are arranged in a circular pattern, and all circumferentially adjacent magnets within the circular pattern have opposite polarities.

In some implementations, the actuator further includes a cover plate that can be secured to the magnet plate that defines the recesses to retain the magnets within the recesses.

In some implementations, the region of the base that together with the membrane defines the fluid pump chamber is a recessed region of the base.

In some implementations, the member has a substantially flat surface that abuts a substantially flat surface of the actuator.

In some implementations, the member is attached to the membrane of the cassette.

In some implementations, the member includes a first portion and multiple resilient legs extending from the first portion.

In some implementations, the base defines channels configured to receive the legs to hold the member in a desired position within the chamber.

In some implementations, the resilient legs collapse when a force of at least about 2.0 lbf is applied to the member in the direction of the rigid base.

In some implementations, the first portion is substantially dome-shaped.

In some implementations, the actuator and the member can be magnetically coupled together with a force of at least about 10 lbf (e.g., at least about 15 lbf, about 10 lbf to about 22 lbf).

In some implementations, the magnetic attraction between the member and the actuator is sufficient to create a vacuum pressure of about 150 mbar to about 200 mbar within the fluid pump chamber when the actuator is retracted.

In some implementations, the actuator can be retracted a sufficient distance away from the base of the cassette to decouple the actuator from the member.

In some implementations, the medical fluid pumping machine includes a feature that is arranged to be received in a bore at least partially formed by the actuator as the actuator is retracted, and the feature can prevent movement of the member in a direction of the retracting piston to facilitate decoupling of the actuator from the member.

In some implementations, the medical fluid pumping machine includes a post that is arranged to be received in a bore formed by the actuator as the actuator is retracted, and the post can prevent movement of the member in a direction of the retracting piston to facilitate decoupling of the actuator from the member.

In some implementations, the membrane together with the base further defines a flow pathway that leads from the fluid pump chamber to an inlet of the cassette and a flow pathway that leads from the fluid pump chamber to an outlet of the cassette.

In some implementations, the medical fluid pumping machine includes first and second actuators, and the membrane and regions of the base cooperate to define first and second fluid pump chambers. The cassette is positionable within the cassette enclosure of the medical fluid pumping machine so that the first and second actuators substantially align with the first and second fluid pump chambers, and first and second members are disposed within the first and second fluid pump chambers, respectively. The members are magnetically attracted to the actuators when the cassette is disposed within the cassette enclosure.

In some implementations, the base of the cassette is a molded fray-like base.

In some implementations, the membrane is attached only to a perimeter region of the base.

In some implementations, the base includes a planar surface and multiple raised features extending from the planar surface, and the plurality of raised features contact the inner surface of the membrane when the membrane is pressed against the base.

In some implementations, at least one of the raised features cooperates with the membrane to form the fluid pump chamber when the membrane is pressed against the base.

In some implementations, at least some of the raised features cooperate with the membrane to form fluid pathways in fluid communication with the fluid pump chamber when the membrane is pressed against the base.

In some implementations, the medical fluid pumping system further includes a cover that releasably attaches to the cassette. The cover includes a projection that holds the member in contact with or in near contact with the base of the cassette when the cover is attached to the cassette.

In some implementations, the medical fluid pumping system is a dialysis system (e.g., a peritoneal dialysis system).

In some implementations, the medical fluid cassette is disposable.

In some implementations, magnetically coupling the actuator to the member includes advancing the actuator toward the medical fluid cassette.

In some implementations, the actuator includes one or more magnets and the member includes a material that is attracted to the one or more magnets.

In some implementations, the medical fluid delivery method further includes advancing the actuator toward the medical fluid cassette to expel fluid from the fluid pump chamber.

In some implementations, the medical fluid delivery method further includes retracting the actuator a sufficient distance to decouple the actuator from the member.

In some implementations, the medical fluid delivery method further includes inhibiting movement of the member in the direction in which the actuator is retracting to facilitate decoupling of the actuator from the member.

In some implementations, inhibiting movement of the member includes drawing the member against a fixed feature that extends into a bore at least partially formed by the actuator.

In some implementations, the fluid pump chamber is formed between a membrane and a base of the cassette, and retracting the actuator and the member causes a portion of the membrane disposed between the actuator and the member to retract.

In some implementations, the medical fluid delivery method further includes expelling the medical fluid from the fluid pump chamber by applying an inward force to an outer surface of the portion of the membrane overlying the fluid pump chamber.

In some implementations, by applying the outward force to the inner surface of the portion of the membrane overlying the fluid pump chamber, a vacuum pressure of about 150 mbar to about 200 mbar is created within the fluid pump chamber.

In some implementations, an outward force of about 20N to about 100N is applied to the membrane by the member.

In some implementations, the medical fluid includes dialysis solution.

In some implementations, the piston head includes an electromagnet.

In some implementations, the system is configured to apply electric current to the electromagnet in a first direction to cause a magnetic attraction between the piston head and the membrane.

In some implementations, the system is configured to apply electric current to the electromagnet in a second direction to cause a repellant force between the piston head and the membrane.

In some implementations, the piston head is substantially dome-shaped.

In some implementations, the membrane includes a body and a layer of magnetically attractive material secured to the body.

In some implementations, the magnetically attractive material is restricted to a portion of the membrane overlying the fluid pump chamber.

In some implementations, the medical fluid pumping machine includes first and second piston heads, and the membrane and regions of the base cooperate to define first and second fluid pump chambers. The cassette is positionable within the cassette enclosure of the medical fluid pumping machine so that the first and second piston heads substantially align with the first and second fluid pump chambers, and the membrane is magnetically attracted to the first and second piston heads when the cassette is disposed within the cassette enclosure.

In some implementations, the medical fluid delivery method further includes applying a first electric current to an electromagnet of the piston head to cause a magnetic attraction between the piston head and the membrane.

In some implementations, the medical fluid delivery method further includes applying a second electric current, opposite to the first electric current, to the electromagnet of the piston head to cause the piston head to repel the membrane.

In some implementations, magnetically coupling the piston head to the membrane includes advancing the piston head toward the medical fluid cassette.

Implementations can include one or more of the following advantages.

In certain implementations, the member disposed in the chamber is attracted to (e.g., magnetically attracted to) the actuator such that the member moves in unison with the actuator, which is positioned on the opposite side of the cassette membrane from the member. As a result, when the actuator is retracted, the member applies an outward force to the inner surface of the membrane causing the volume of the fluid pump chamber to increase and drawing medical fluid into the fluid pump chamber. This arrangement allows the fluid to be drawn into the fluid pump chamber without requiring vacuum pressure to be applied to the outside of the membrane. As a result, the complexity and cost of the medical fluid pumping machine can be reduced, and the noise levels resulting from operation of the machine can be reduced relative to vacuum-based systems.

In some implementations, the medical fluid pumping machine and the medical fluid cassette are configured such that the actuator can be automatically decoupled from the member in the fluid pump chamber of the cassette. Automatic decoupling of the actuator from the member can, for example, be achieved by holding the cassette membrane and the member in place while retracting the actuator. As a result of this automatic decoupling, the user can simply remove the cassette from the cassette compartment of the medical fluid pumping machine upon completion of treatment without having to take additional time and make additional effort to manually decouple the member from the actuator.

In certain implementations, the member disposed within the fluid pump chamber is shaped to conform to the inner surface of the fluid pump chamber. The conforming shapes of the member and the fluid pump chamber can help to increase pumping accuracy of the medical fluid pumping system.

In some implementations, the member is retained in a substantially centered position within the pump chamber. This arrangement can help to increase the volumetric accuracy with which the medical fluid pumping system is able to deliver fluid during a treatment cycle.

In certain implementations, the actuator includes an array of magnets that are arranged in an alternating polarity pattern. For example, the magnets can be arranged in one or more substantially circular patterns such that all circumferentially adjacent magnets within the circumferential pattern (s) have opposite polarity. As a result of this arrangement, the magnetic field external to the medical fluid pumping machine can be reduced or minimized while maintaining a desired magnetic force at the surface of the actuator.

In some implementations, the actuator includes an array of recesses in which magnets can be retained and the actuator can be easily disassembled to insert magnets into or remove magnets from the actuator. By placing a desired number of magnets within the recesses of the actuator, a desired magnetic attraction between the actuator and the associated member disposed within the pump chamber can be achieved. Thus, in implementations where the actuator can be easily disassembled and reassembled to add or remove magnets, the magnetic force of the actuator can easily be tailored to a particular application.

In certain implementations, the actuator and the member disposed in the fluid pump chamber are configured so that the actuator and the member become decoupled from one another when the pulling force of the actuator relative to the member exceeds a certain value. This can help to prevent the vacuum pressure applied to the patient from exceeding a desired limit. For example, this arrangement can help to maintain the vacuum or suction pressure within a desired range in the event that an obstruction or blockage occurs in a delivery line that is fluidly connected to the fluid pump chamber. As an example, if an obstruction or blockage occurs in the patient line leading to the cassette and causes the fluid flow rate into the fluid pump chamber to decrease, the retracting actuator head will separate from the member disposed in the chamber.

In some implementations, the cassette membrane includes a magnetically attractive material such that the membrane itself can be coupled to the actuator during use. In such implementations, the fluid pump chamber of the cassette typically does not include a separate magnetically attractive member disposed therein. Such cassettes can be relatively easy to use and relatively inexpensive to manufacture.

In certain implementations, the actuator is equipped with an electromagnet such that the magnetic attraction between the actuator and the magnetically attractive member or magnetically attractive membrane of the cassette can be controlled as desired. In such implementations, for example, the electromagnet can be activated after the cassette has been properly aligned. This can help to ensure that the actuator is properly aligned with the fluid pump chamber of the cassette during use and can thus increase pumping accuracy. In some implementations, the electromagnet is deactivated prior to removing the cassette from the medical fluid pumping machine. This can make removal of the cassette from the machine easier while decreasing the risk of tearing the membrane during the decoupling process. Similarly, the strength of the electromagnet can be modulated to adjust the strength of the magnetic attraction between the actuator and the magnetically attractive member or magnetically attractive membrane of the cassette for a given situation.

In implementations in which the magnetically attractive member or magnetically attractive membrane of the cassette produces its own magnetic field, the current delivered to the electromagnet can be reversed prior to removing the cassette from the machine. Reversing the current in this manner can cause the actuator to repel the magnetically attractive member or magnetically attractive membrane of the cassette, which can facilitate the decoupling and removal process and reduce the risk of damage to the membrane.

Other aspects, features, and advantages will be apparent from the description and drawings, and from the claims.

DETAILED DESCRIPTION

In certain aspects of the invention, a medical fluid cassette (e.g., a dialysis fluid cassette) includes a member disposed in a fluid pump chamber formed between a membrane and a base of the cassette. The medical fluid cassette is configured to be disposed in a cassette compartment of a medical fluid pumping machine (e.g., a dialysis machine) in a manner such that an actuator of the medical fluid pumping machine is substantially aligned with the fluid pump chamber. The member is attractive (e.g., magnetically attractive) to the actuator such that the actuator and the member can be coupled together with a flexible membrane of the cassette compressed therebetween. During use, the actuator is advanced to apply an inward force to the membrane and the member, forcing fluid out of the fluid pump chamber. Due to the attraction between the member and the actuator, the member and the actuator become coupled together as the actuator is advanced and the cassette membrane becomes compressed between the member and the actuator. The actuator is subsequently retracted causing the member disposed in the fluid pump chamber to retract and apply an outward force to the membrane. This increases the volume of the fluid pump chamber, causing fluid to be drawn into the chamber. By coupling the member to the actuator in this manner, the volume of the fluid pump chamber can be increased by simply retracting the actuator. There is typically no need for an external vacuum to be applied to the cassette membrane to increase the volume of the fluid pump chamber. Exemplary medical fluid cassettes, medical fluid pumping machines, medical fluid pumping systems, and medical fluid delivery methods are described below.

Figure 1:
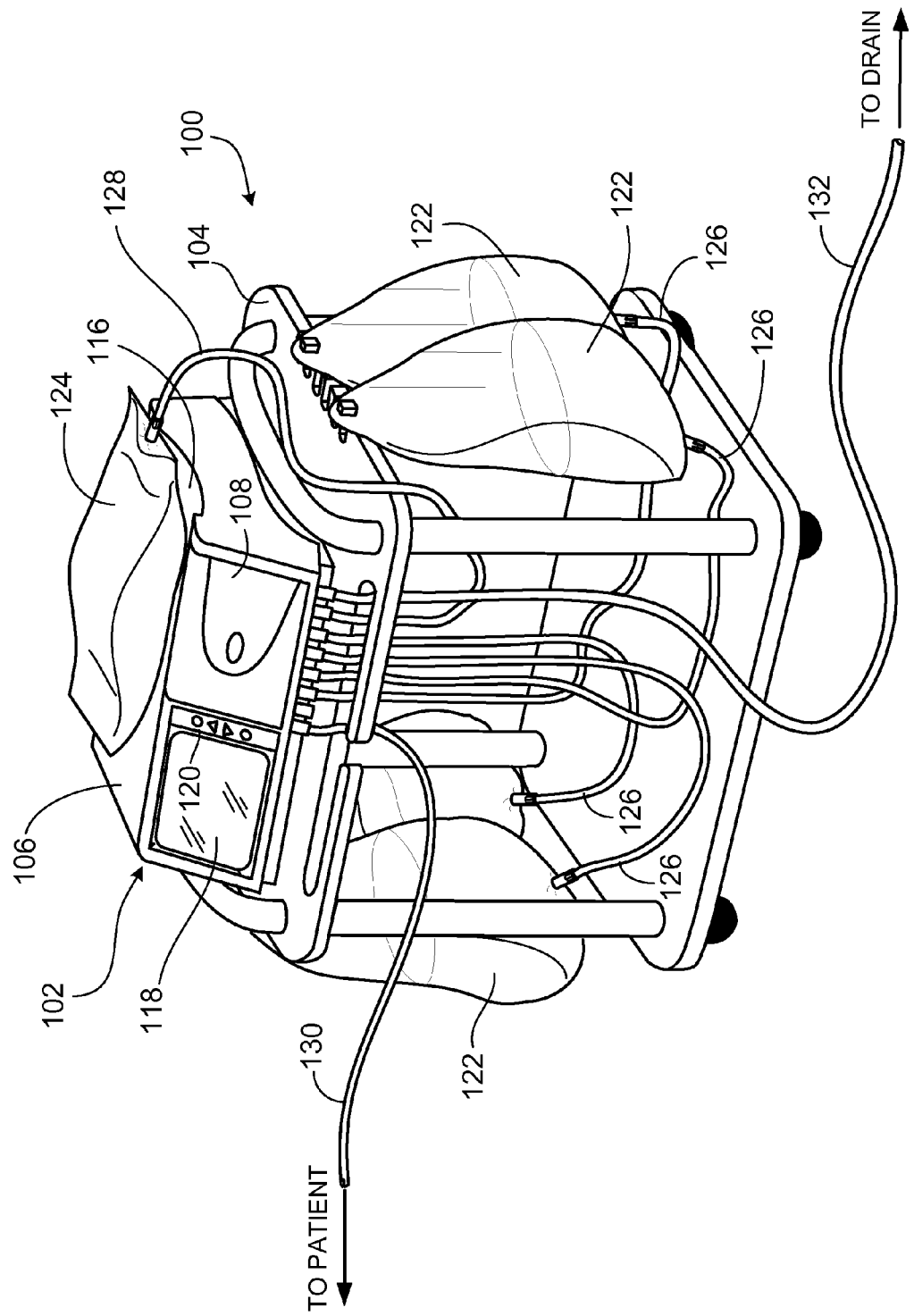
FIG. 1 is a perspective view of a peritoneal dialysis ("PD") system that includes a PD cycler positioned atop a portable cart.
Figure 2:
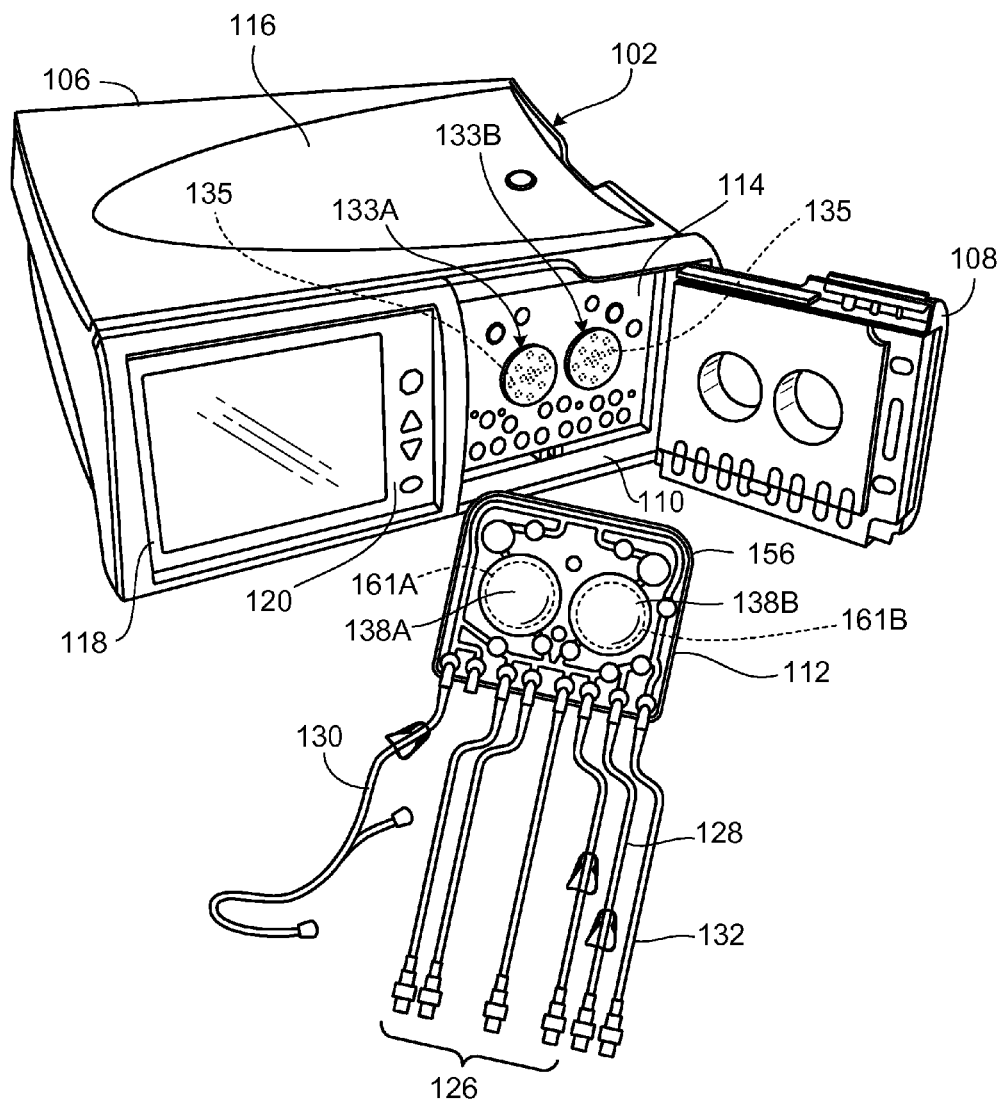
FIG. 2 is a perspective view of the PD cycler and PD cassette of the PD system of FIG. 1. A door of the PD cycler is in the open position to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that mates with a disposable PD cassette 112 when the cassette 112 is disposed within a cassette compartment 114 formed between the cassette interface 110 and the closed door 108. The cassette 112, as will be described in greater detail below, includes fluid pump chambers 138A, 138B formed between a rigid base 156 and a flexible membrane 140 (shown in FIGS. 5 and 7). Magnetically attractive dome-shaped members 161A, 161B are disposed in the fluid pump chambers 138A, 138B.

A heater tray 116 is positioned on top of the housing 106. The heater tray 116 is sized and shaped to accommodate a bag of dialysis solution (e.g., a five liter bag of dialysis solution). The PD cycler 102 also includes a touch screen 118 and additional control buttons 120 that can be operated by a user (e.g., a patient) to allow, for example, set-up, initiation, and/or termination of a PD treatment.

Still referring to FIG. 1, dialysis solution bags 122 are suspended from fingers on the sides of the cart 104, and a heater bag 124 is positioned on the heater tray 116. The dialysis solution bags 122 and the heater bag 124 are connected to the cassette 112 (shown in FIG. 2) via dialysis solution bag lines 126 and a heater bag line 128, respectively. The dialysis solution bag lines 126 can be used to pass dialysis solution from the dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
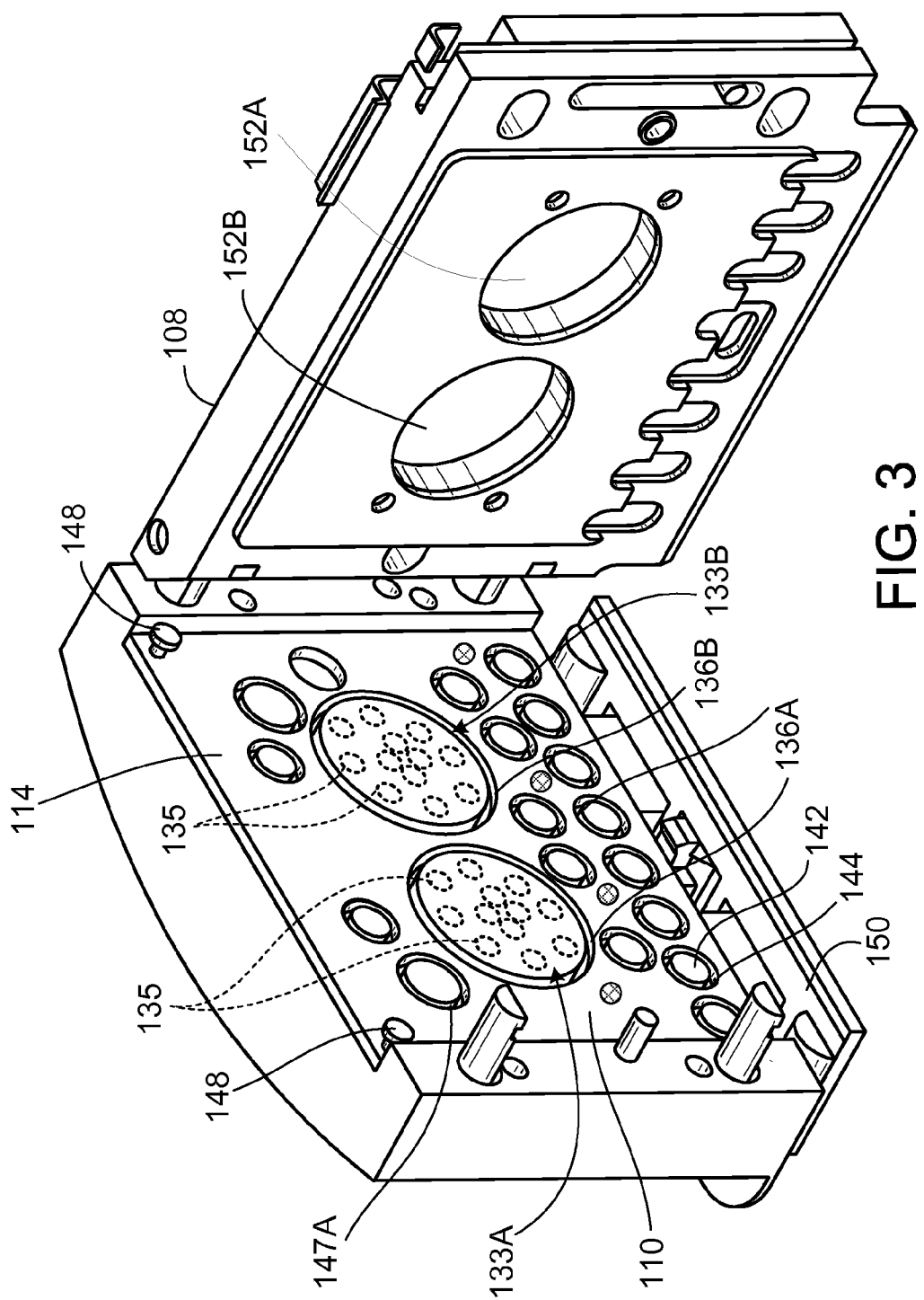
FIG. 3 is a perspective view of an open cassette compartment of the PD cycler of FIGS. 1 and 2.

FIG. 3 shows a more detailed view of the cassette interface 110 and the door 108 of the PD cycler 102. As shown, the PD cycler 102 includes actuators (also referred to as pistons) 133A, 133B that contain multiple magnets 135. The actuators 133A, 133B are connected to a motor (e.g., a stepper motor) positioned in the housing 106 of the PD cycler 102 so that the actuators 133A, 133B can be axially moved within actuator access ports 136A, 136B formed in the cassette interface 110. As described in greater detail below, the magnetic actuators 133A, 133B can be coupled to the magnetically attractive dome-shaped members 161A, 161B of the cassette 112 when the cassette 112 is disposed within the cassette enclosure 114 during use such that the dome-shaped members 161A, 161B can be reciprocated along with the actuators 133A, 133B.

Figure 4:
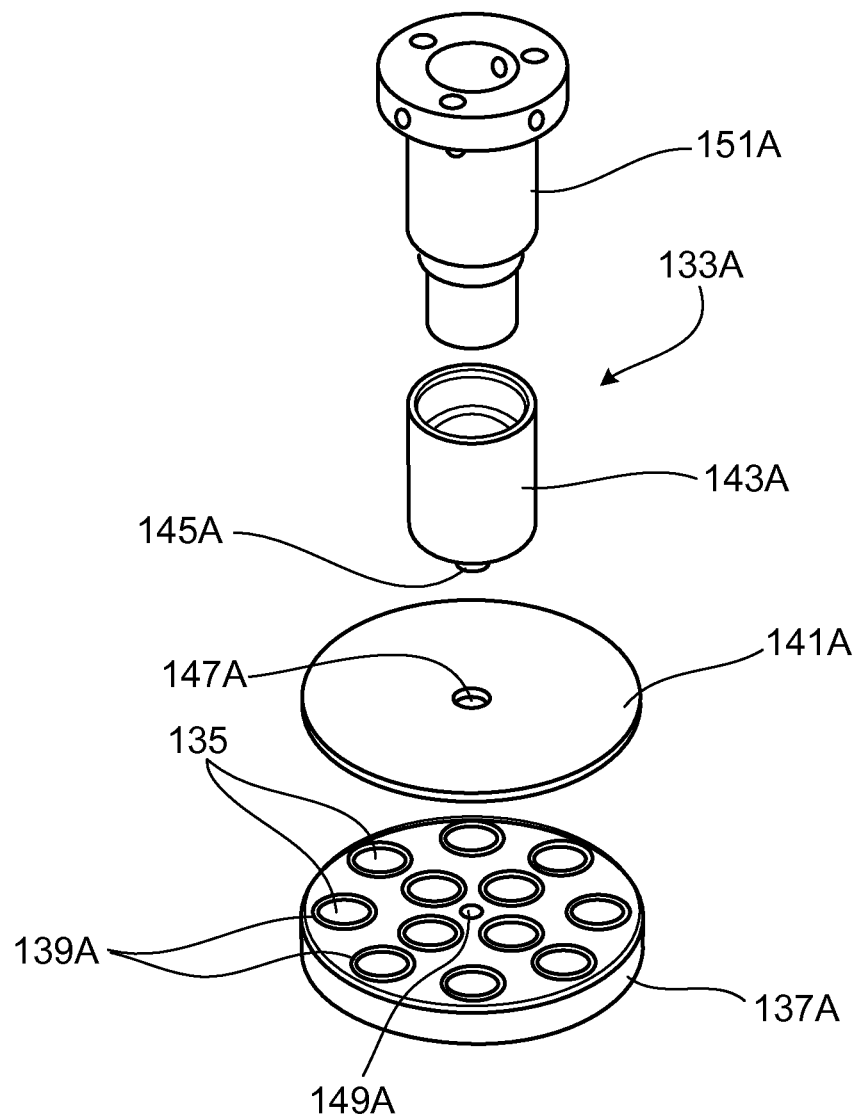
FIG. 4 is an exploded, perspective view of a magnetic actuator assembly of the PD system of FIG. 1.

FIG. 4 illustrates an exploded view of the actuator 133A. Only the actuator 133A will be described here since the other actuator 133B has the same construction and operates in the same way as the actuator 133A. As shown in FIG. 4, the actuator 133A includes a magnet plate 137A that has a concentric circular array of recesses 139A in which the magnets 135 are disposed. A cap plate 141A is disposed over the back side of the magnet plate 137A in order to hold the magnets 135 within the recesses 139A of the magnet plate 137A. An adaptor 143A includes a threaded stem 145A that is inserted through a central bore 147A in the cap plate 141A and matingly engages a threaded bore 149A in the magnet plate 137A to secure the cap plate 141A to the magnet plate 137A. A plunger shaft 151A of the actuator 133A is secured at one end to the adapter 143A and at its opposite end to the motor in the housing 106 of the PD cycler 102. Any of various mechanical coupling techniques can be used to secure the plunger shaft 151A to the adapter 143A. Similarly, any of various suitable connection mechanisms, such as lead screw mechanisms, ball screw mechanisms, or other gear-type mechanisms, can be used to connect the plunger shaft 151A to the motor. Operation of the motor causes the actuator 133A to reciprocate within the actuator access port 136A formed in the cassette interface 110 (shown in FIG. 3).

Figure 12:
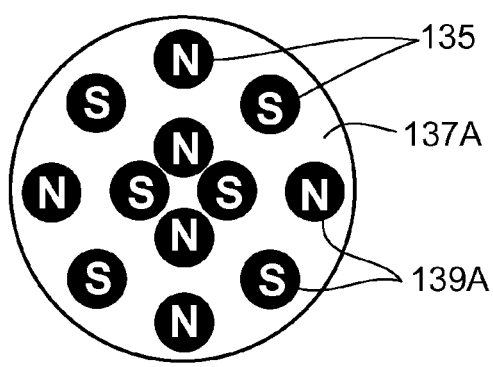
FIGS. 12-16 illustrate various magnet arrangements for the actuators of the PD cycler of the PD system of FIG. 1.
Figure 13:
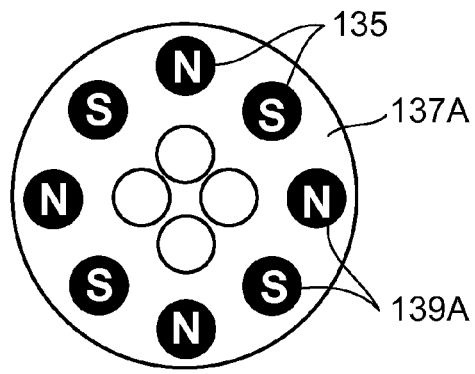
Figure 14:
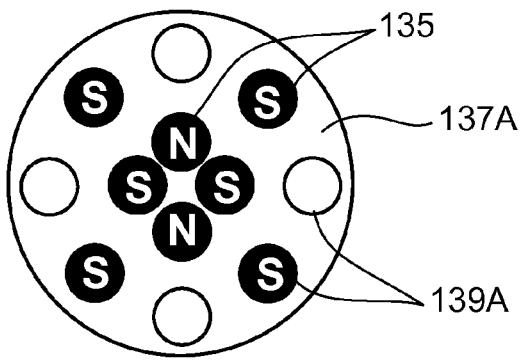
Figure 15:
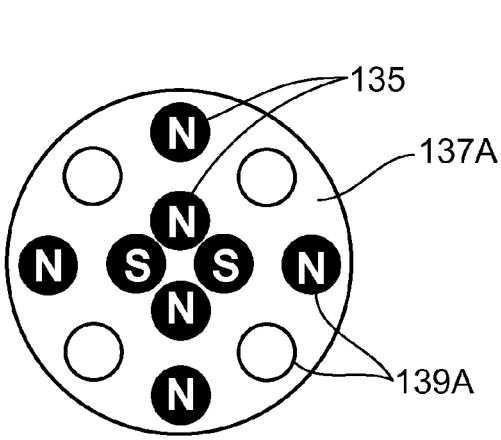
Figure 16:
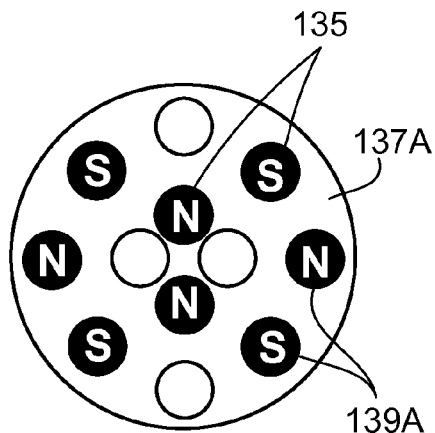

Referring briefly to both FIGS. 4 and 12, one magnet 135 is disposed within each of the recesses 139A to form one circular grouping of magnets located near the center of the magnet plate 137A and another circular grouping of magnets positioned around a circumferential edge region of the magnet plate 137A. Every other magnet around each of the substantially circular magnet groupings has opposite polarity such that circumferentially adjacent magnets within the groupings have opposite polarities. It has been found that this arrangement of alternating polarity advantageously decreases the magnetic field present external to the PD cycler 102. The magnetic field typically has a strength of less than 10 Gauss (e.g., less than 5 Gauss) at a distance of about 1.5 inches in front of the actuator 133A.

The magnet plate 137A, the cap plate 141A, the adapter 143A, and the plunger shaft 151A are typically formed of one or more non-magnetic materials. In some implementations, these actuator components are formed of aluminum. Other metals, such as brass, bronze, non-magnetic stainless steel, and titanium, can alternatively or additional be used to form the magnet plate 137A, the cap plate 141A, the adapter 143A, and/or the plunger shaft 151A. Alternatively, certain plastics, such as ABS, Delrin, polycarbonate, PEEK, fiber-reinforced PEEK, carbon fiber, nylon, Ultem, PVC, and PPC, can be used to form the magnet plate 137A, the cap plate 141A, the adapter 143A, and/or the plunger shaft 151A.

The magnet plate 137A and cap plate 141A of the actuator 133A generally have diameters that are substantially equal to the diameter of the associated dome-shaped member 161A disposed within the pump chamber 138A of the cassette 112. In some implementations, the magnet plate 137A and cap plate 141A have diameters of about 1.0 inch to about 3.0 inch (e.g., about 2.0 inch). The magnet plate 137A has a large enough thickness so that the recesses 139A formed in the magnet plate 137A can accommodate the magnets 135. The front wall portion of the magnet plate 137A that sits adjacent each magnet 135 is sufficiently thin so that the magnetic force of the magnets 135 can penetrate through the front wall of the magnet plate 137A and allow the actuator 133A to be coupled to the dome-shaped member 161A with a desired force (e.g., at least about 10 lbf, at least about 15 lbf, about 10 lbf to about 22 lbf). In some implementations, the magnet plate 137A has a thickness of about 0.20 inch to about 0.30 inch (e.g., about 0.25 inch), and the recesses formed in the magnet plate 137A have diameters of about 0.35 inch to about 0.45 inch (e.g., about 0.38 inch) and depths of about 0.195 inch to about 0.295 inch (e.g., about 0.245 inch). In certain implementations, the thickness of the front wall of the magnet plate 137A in the areas overlying the recesses 139A is about 0.005 inch. Using such a thin wall in the areas overlying the recesses 139A can help to ensure that a desired amount of magnetic force extends beyond the front face of the actuator 133A.

The magnets 135 can be any of various different types of magnets that are together capable of providing the desired coupling force between the actuator 133A and the dome-shaped member 161A of the cassette 112. In certain implementations, the magnets are formed of NdFeB and plated with NiCuNi. Each of the magnets can have a diameter of about 0.345 inch to about 0.445 inch (e.g., about 0.375 inch) and a thickness of about 0.075 inch to about 0.175 inch (e.g., about 0.125 inch). Suitable magnets are available from K&J Magnetics, Inc., under product number D62-N52.

As will be discussed in greater below, when the cassette 112 (shown in FIGS. 5-7) is positioned within the cassette compartment 114 and the door 108 is closed, the magnetic actuators 133A, 133B of the PD cycler 102 align with pump chambers 138A, 138B of the cassette 112 such that the magnetically attractive dome-shaped members 161A, 161B disposed in the chambers 138A, 138B become magnetically coupled to the actuators 133A, 133B with portions of the cassette membrane 140 that overlie the pump chambers 138A, 138B compressed between the actuators 133A, 133B and the dome-shaped members 161A, 161B. The actuators 133A, 133B, the dome-shaped members 161A, 161B, and the portions of the cassette membrane 140 compressed therebetween can be advanced to decrease the volume defined by the pump chambers 138A, 138B and force dialysis solution out of the pump chambers 138A, 138B. The actuators 133A, 133B, the dome-shaped members 161A, 161B, and the portions of the cassette membrane 140 compressed therebetween can then be retracted to decrease the volume defined by the pump chambers 138A, 138B and draw dialysis solution into the pump chambers 138A, 138B.

Referring again to FIG. 3, the PD cycler 102 also includes multiple inflatable members 142 positioned within inflatable member access ports 144 in the cassette interface 110. The inflatable members 142 align with depressible dome regions 146 of the cassette 112 (shown in FIGS. 5-7) when the cassette 112 is positioned within the cassette compartment 114. While only one of the inflatable members 142 is labeled in FIG. 3, it should be understood that the PD cycler 102 includes an inflatable member 142 associated with each of the depressible dome regions 146 of the cassette 112. The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be occluded. Thus, dialysis solution can be pumped through the cassette 112 by actuating the actuators 133A, 133B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a lower ledge 150 extending from the cassette interface 110 to allow the door 108 to be closed over the cassette 112. The locating pins 148 help to ensure that the pump chambers 138A, 138B of the cassette 112 are aligned with the actuators 133A, 133B when the cassette 112 is positioned in the cassette compartment 114 between the closed door 108 and the cassette interface 110.

The door 108, as shown in FIG. 3, defines recesses 152A, 152B that substantially align with the actuators 133A, 133B when the door 108 is in the closed position. When the cassette 112 is positioned within the cassette compartment 114, hollow projections 154A, 154B of the cassette 112 (shown in FIG. 6), inner surfaces of which cooperate with the membrane 140 to form the pump chambers 138A, 138B, fit within the recesses 152A, 152B. The door 108 further includes a pad that can be inflated during use to compress the cassette 112 between the door 108 and the cassette interface 110. With the pad inflated, the portions of the door 108 forming the recesses 152A, 152B support the projections 154A, 154B and the planar surface of the door 108 supports the other regions of the cassette 112. The door 108 can counteract the forces applied by the actuators 133A, 133B and the inflatable members 142 and thus allows the actuators 133A, 133B to depress the portions of the membrane 140 overlying the pump chambers 138A, 138B and similarly allows the inflatable members 142 to actuate the depressible dome regions 146 on the cassette 112.

The PD cycler 102 includes various other features not described in detail herein. Further details regarding the PD cycler 102 and its various components can be found in U.S. Patent Application Publication No. 2007/0112297, which is incorporated by reference herein.

Figure 5:
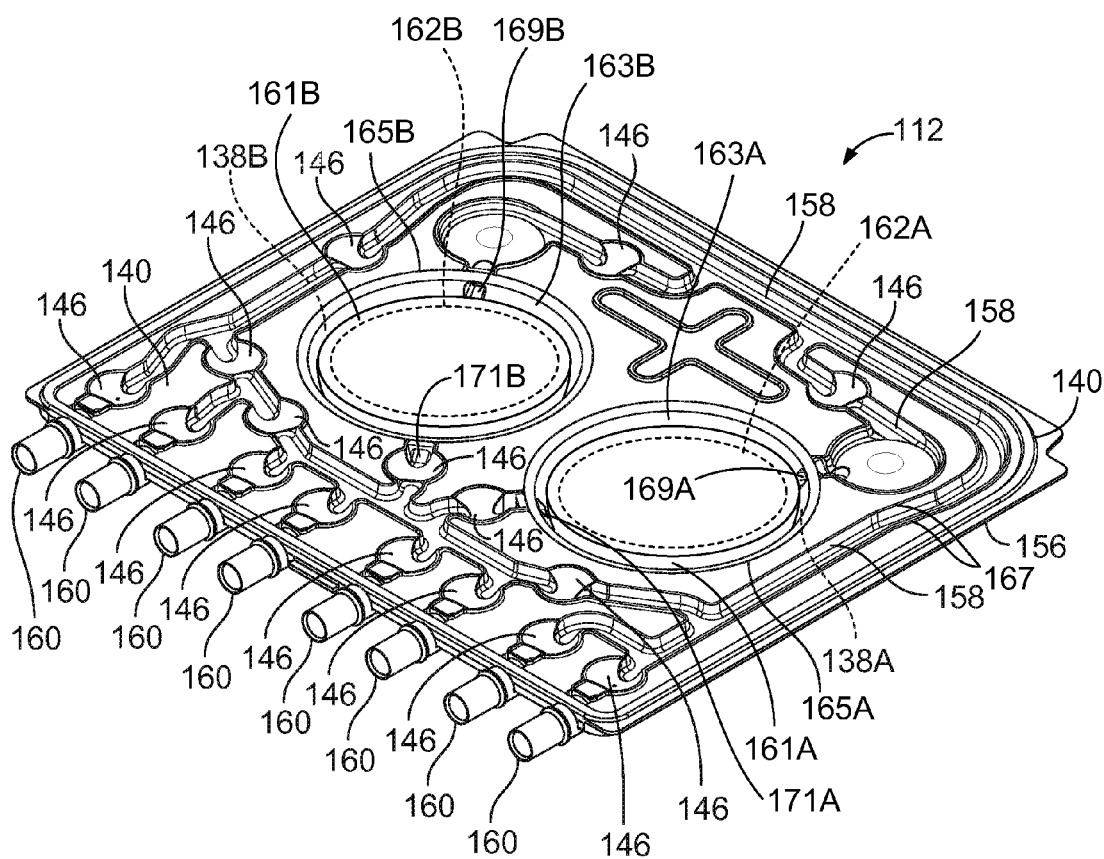
FIGS. 5 and 6 are perspective views of the PD cassette of the PD system of FIG. 1, from a flexible membrane side of the PD cassette and from a rigid base side of the PD cassette, respectively. The PD cassette includes magnetically attractive dome-shaped members disposed in pump chambers formed between the membrane and the rigid base of the cassette.
Figure 6:
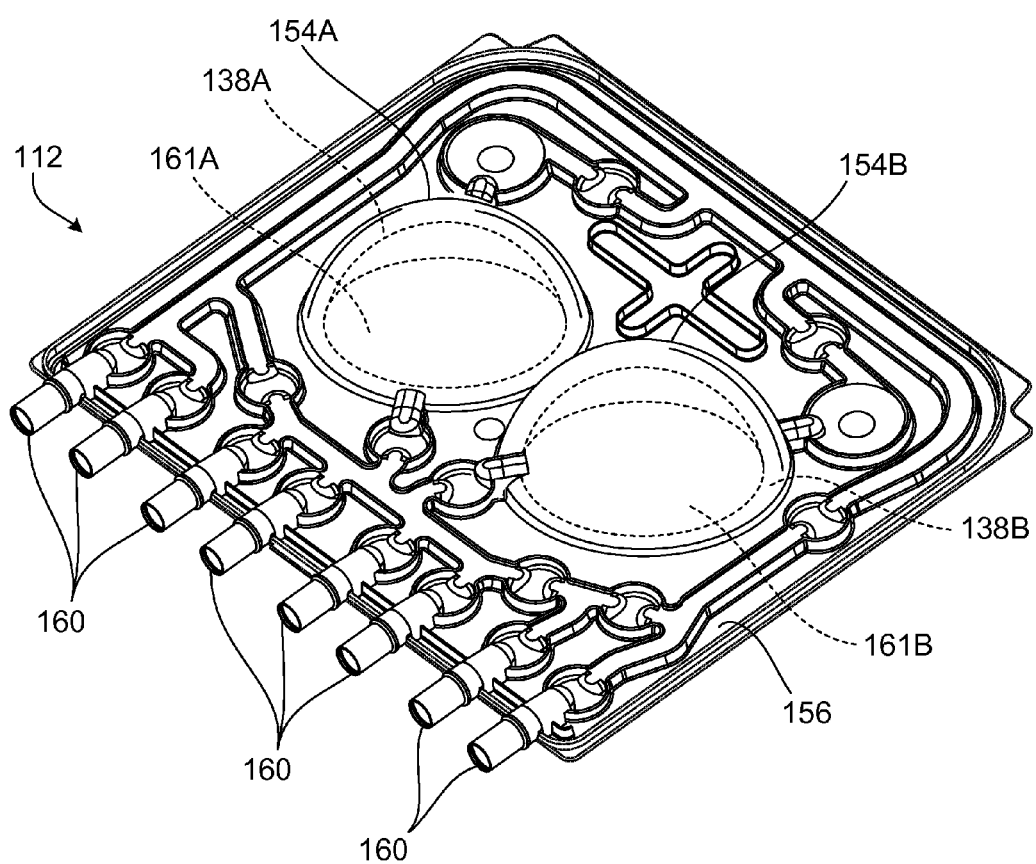
Figure 7:
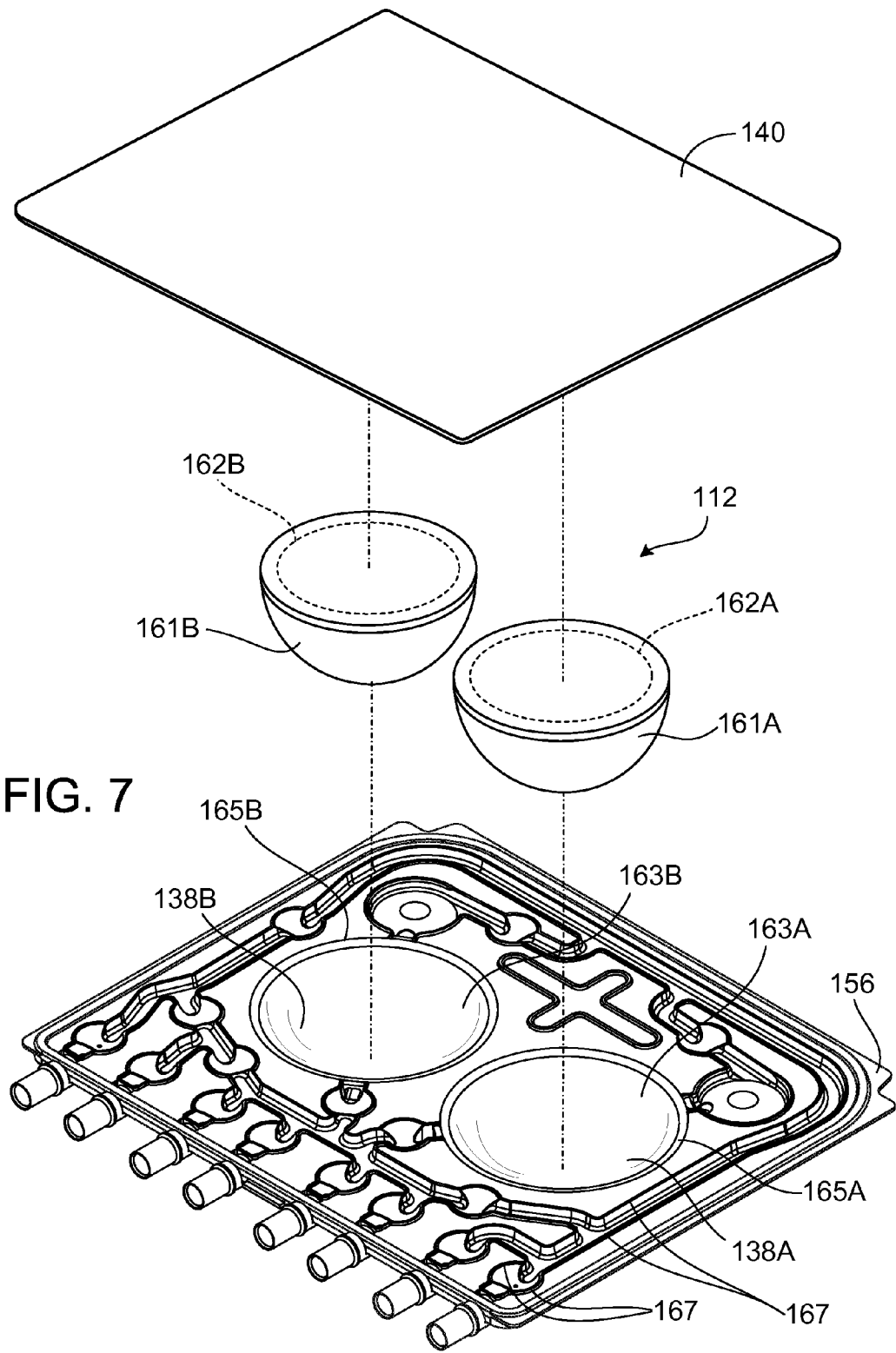
FIG. 7 is an exploded, perspective view of the PD cassette of the PD system of FIG. 1.

FIGS. 5 and 6 are perspective views from the membrane side and rigid base side, respectively, of the cassette 112, and FIG. 7 is an exploded, perspective view of the cassette 112. As shown in FIGS. 5-7, the cassette 112 includes the tray-like rigid base 156, the flexible membrane 140, which is attached to the periphery of the base 156, and the magnetically attractive dome-shaped members 161A, 161B, which are disposed in recessed regions 163A, 163B formed by the hollow projections 154A, 154B of the base 156. The recessed regions 163A, 163B of the base 156 cooperate with the flexible membrane 140 to form the pump chambers 138A, 138B when the cassette 112 is compressed between the door 108 and the cassette interface 110 of the PD cycler 102 resulting in the flexible membrane 140 being pressed against raised ridges 165A, 165B that extend from the base 156 and surround the recessed regions 163A, 163B. In particular, the volumes between the membrane 140 and the hollow projections 154A, 154B that form the recessed regions 163A, 163B of the base 156 serve as the pump chambers 138A, 138B.

Flat rear surfaces of the dome-shaped members 161A, 161B are attached (e.g., thermally or adhesively bonded) to the inner surface of portions of the membrane 140 overlying the pump chambers 138A, 138B. The dome-shaped members 161A, 161B are shaped to generally conform to the recessed regions 163A, 163B of the base 156 of the cassette 112.

The dome-shaped members 161A, 161B include internal magnetically attractive, steel plates 162A, 162B that cause the dome-shaped members 161A, 161B to be attracted to the magnetic actuators 133A, 133B of the PD cycler 102. Due to this construction, the actuators 133A, 133B can be used to advance the dome-shaped members 161A, 161B toward the base 156 and thus decrease the volume of the pump chambers 138A, 138B, or to retract the dome-shaped members 161A, 161B away from the base 156 of the cassette 112 and thus decrease the volume of the pump chambers 138A, 138B. Decreasing the volume of the pump chambers 138A, 138B causes fluid (e.g., about 12-13 ml of fluid) to be expelled from the pump chambers 138A, 138B via fluid outlet ports 169A, 169B, while increasing the volume of the pump chambers 138A, 138B causes fluid (e.g., about 12-13 ml of fluid) to be drawn into the pump chambers 138A, 138B via fluid inlet ports 171A, 171B.

Figure 8:
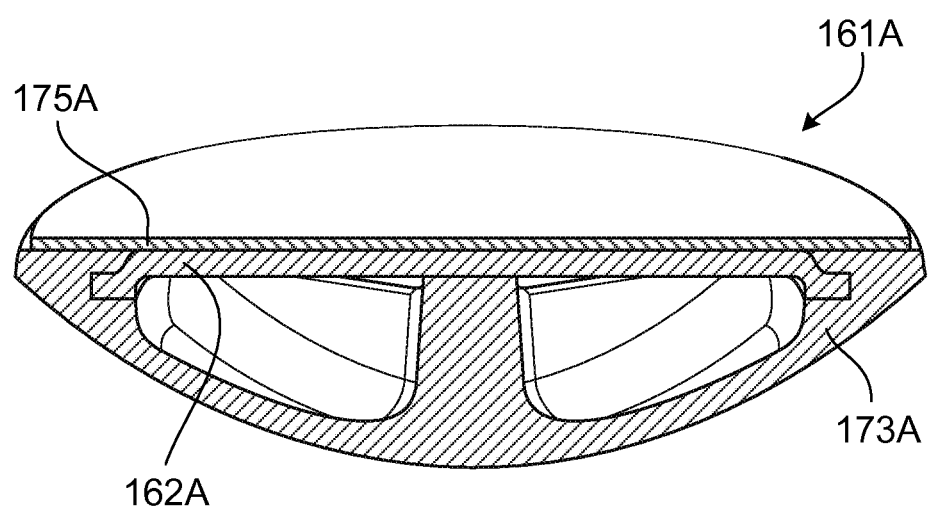
FIG. 8 is a perspective, cross-sectional view of one of the magnetically attractive dome-shaped members of the PD cassette of the PD system of FIG. 1.

FIG. 8 shows a perspective, cross-sectional view of the dome-shaped member 161A. The other dome-shaped member 161B is identical to the illustrated dome-shaped member 161A and thus, for simplicity, is not shown here. As shown in FIG. 8, the dome-shaped member 161A includes a dome-shaped polypropylene portion 173A, a polypropyline biofine film 175A, and the magnetically attractive steel plate 162A sealed between the polypropylene portion 173A and the polypropylene film 175A. The polypropylene materials used for the dome-shaped portion 173A and the film 175A are biocompatible. Due to the construction of the dome-shaped member 161A, bodily fluids of a patient will only contact the biocompatible polypropylene portion 173A and the biocompatible polypropylene film 175A, and not the steel plate 162A.

To construct the dome-shaped member 161A, a pre-form of the dome-shaped portion 173A is first formed using an injection molding technique. The steel plate 162A is then positioned within a recess of the pre-form of the dome-shaped portion 173A, and the assembly of steel plate 162A and the preform are subjected to an overmolding technique in which the steel plate 162A is disposed and securely held within a mold into which molten polypropylene is injected. The injected molten polypropylene is allowed to solidify and form the remainder of the dome-shaped portion 173A, which partially encapsulates the steel plate 162A. The circumferential region of the steel plate 162A, as shown in FIG. 8, is deformed away from the plane of the main portion of the plate such that the molten polypropylene is allowed to flow around and encapsulate the circumferential region of the steel plate 162A to securely retain the steel plate 162A. The polypropylene film 175A is then placed over the steel plate 162A and the dome-shaped portion 173A, and the circumferential edge region of the polypropylene film 175A is laser welded to the circumferential edge region of the dome-shaped polypropylene portion 173A. This laser weld creates a liquid-tight seal and thus seals the steel plate 162A in a liquid-tight manner between the polypropylene film 175A and the dome-shaped polypropylene portion 173A.

As an alternative to using overmolding to secure the steel plate 162A to the dome-shaped polypropylene portion 173A, any of various mechanical coupling techniques, such as screwing the steel plate 162A to the dome-shaped polypropylene portion 173A and snap fitting these components together, can be used. Similarly, as an alternative to using a laser weld to secure the polypropylene film 175A to the dome-shaped polypropylene portion 173A, other thermal bonding techniques that create a suitable bond can be used.

While the dome-shaped portion 173A and the film 175A have been described as being formed of polypropylene, one or more other biocompatible polymers can alternatively or additionally be used. In certain implementations, one or both of these components are formed of polyoxymethylene (marketed under the trade name Delrin available from Dupont of Wilmington, Del.). Other suitable biocompatible polymers include polytetrafluoroethylene (PTFE), polyvinyl chloride, polycarbonate, and polysulfone.

Similarly, while the magnetically attractive plate 162A has been described as being formed of steel, one or more other ferromagnetic materials can alternatively or additionally be used. Other examples of ferromagnetic materials from which the magnetically attractive plate 162A can be formed include stainless steel, iron, nickel, and cobalt. The thickness of the magnetically attractive plate 162A depends on the type of material from which the magnetically attractive plate 162A is formed and the desired magnetic force to be applied between the plate 162A and the actuator 133A. In some implementations, the plate 162A has a thickness of about 0.020 inch to about 0.060 inch (e.g., about 0.040 inch). In certain implementations, the magnetically attractive plate 162A is a magnet.

Referring again to FIGS. 5-7, the membrane 140, when compressed against the base 156, also cooperates with a series of raised ridges 167 extending from the base 156 to form a series of fluid pathways 158 and to form the multiple, depressible dome regions 146, which are widened portions (e.g., substantially circular widened portions) of the fluid pathways 158. During use, the dialysis solution flows to and from the pump chambers 138A, 138B through the fluid pathways 158 and dome regions 146. At each depressible dome region 146, the membrane 140 can be deflected to contact the surface of the base 156 from which the raised ridges 167 extend. Such contact can substantially impede (e.g., prevent) the flow of dialysis solution along the region of the pathway 158 associated with that dome region 146 during use. Thus, as described in further detail below, the flow of dialysis solution through the cassette 112 can be controlled through the selective depression of the depressible dome regions 146 by selectively inflating the inflatable members 142 of the PD cycler 102.

The rigidity of the base 156 helps to hold the cassette 112 in place within the cassette compartment 114 of the PD cycler 102 and to prevent the base 156 from flexing and deforming in response to forces applied to the projections 154A, 154B by the dome-shaped members 161A, 161B and in response to forces applied to the planar surface of the base 156 by the inflatable members 142.

The base 156 can be formed of any of various relatively rigid materials. In some implementations, the base 156 is formed of one or more polymers, such as polypropylene, polyvinyl chloride, polycarbonate, polysulfone, and other medical grade plastic materials. In certain implementations, the base 156 is formed of one or more metals or alloys, such as stainless steel. The base 156 can alternatively be formed of various different combinations of the above-noted polymers and metals. The base 156 can be formed using any of various different techniques, including machining, molding, and casting techniques.

Still referring to FIGS. 5-7, fluid line connectors 160 are positioned along the bottom edge of the cassette 112. The fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette 112, as shown in FIGS. 1 and 2, the connectors 160 allow dialysis solution to flow into and out of the cassette 112 during use.

As noted above, the membrane 140 is attached to the periphery of the base 156. The portion of the membrane 140 overlying the central portion of the base 156 is typically not attached to the base 156. Rather, this portion of the membrane 140 sits loosely atop the raised ridges 165A, 165B, and 167 extending from the planar surface of the base 156. Any of various attachment techniques, such as adhesive bonding and thermal bonding, can be used to attach the membrane 140 to the periphery of the base 156. The thickness and material(s) of the membrane 140 are selected so that the membrane 140 has sufficient flexibility to flex toward the base 156 in response to the force applied to the membrane 140 by the actuators 133A, 133B and the inflatable members 142. In certain implementations, the membrane 140 is about 0.100 micron to about 0.150 micron in thickness. However, other thicknesses may be sufficient depending on the type of material used to form the membrane 140.

Any of various different materials that permit the membrane 140 to deflect in response to movement of the actuators 133A, 133B and inflation of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tufted® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

The rigid base 156, the membrane 140, and the dome-shaped members 161A, 161B are typically formed separately and then assembled to make the cassette 112. In some implementations, for example, after forming the rigid base 156 and the dome-shaped members 161A, 161B, the dome-shaped members 161A, 161B are attached (e.g., welded) to the membrane 140 and then inserted into the recesses 163A, 163B formed by the hollow protrusions 154A, 154B of the rigid base 156. The membrane 140 is then attached to the perimeter of the rigid base 156.

Figure 9:
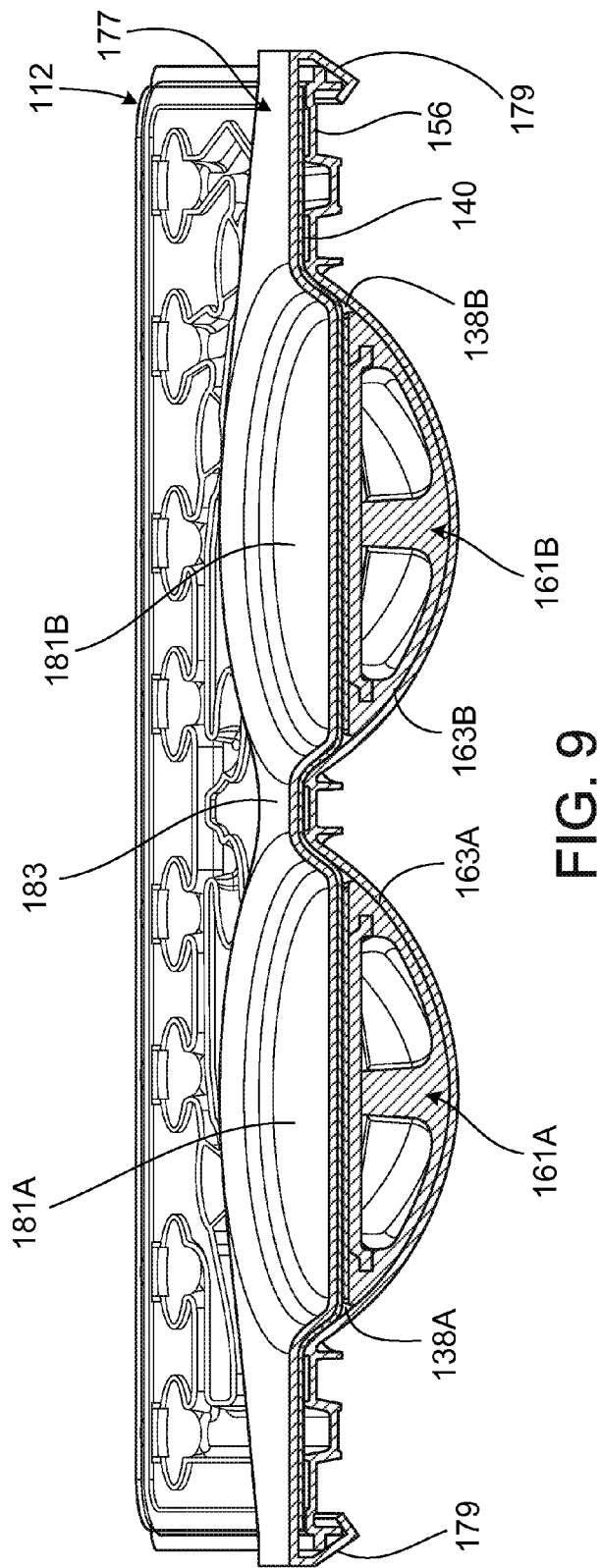
FIG. 9 is a perspective, cross-sectional view of the PD cassette of the PD system of FIG. 1 with a retention cover positioned over the pump chambers to hold the magnetically attractive dome-shaped members in place during shipping.

Referring to FIG. 9, during shipping of the cassette 112, a rigid cover 177 is snapped onto the cassette 112 to hold the dome-shaped members 161A, 161B in place within the pump chambers 138A, 138B. The cover 177 is a rigid polymeric member that has resilient tabs 179 that fit around side edge regions of the cassette 112 to firmly hold the cover against the cassette 112. The cover 177 includes projections 181A, 181B that extend from a relatively planar section 183 of the cover 177 and are sized and shaped to fit within the recessed regions 163A, 163B of the base 156 of the cassette 112. The projections 181A, 181B extend a sufficient distance from the planar section 183 of the cover 177 to press the dome-shaped members 161A, 161B of the cassette 112 against the base 156 of the cassette 112 when the cover is snapped onto the cassette 112. By holding the dome-shaped members 161A, 161B in this state during shipping, the dome-shaped members 161A, 161B are prevented from moving around within the pump chambers 138A, 138B and potentially becoming damaged.

Figure 10:
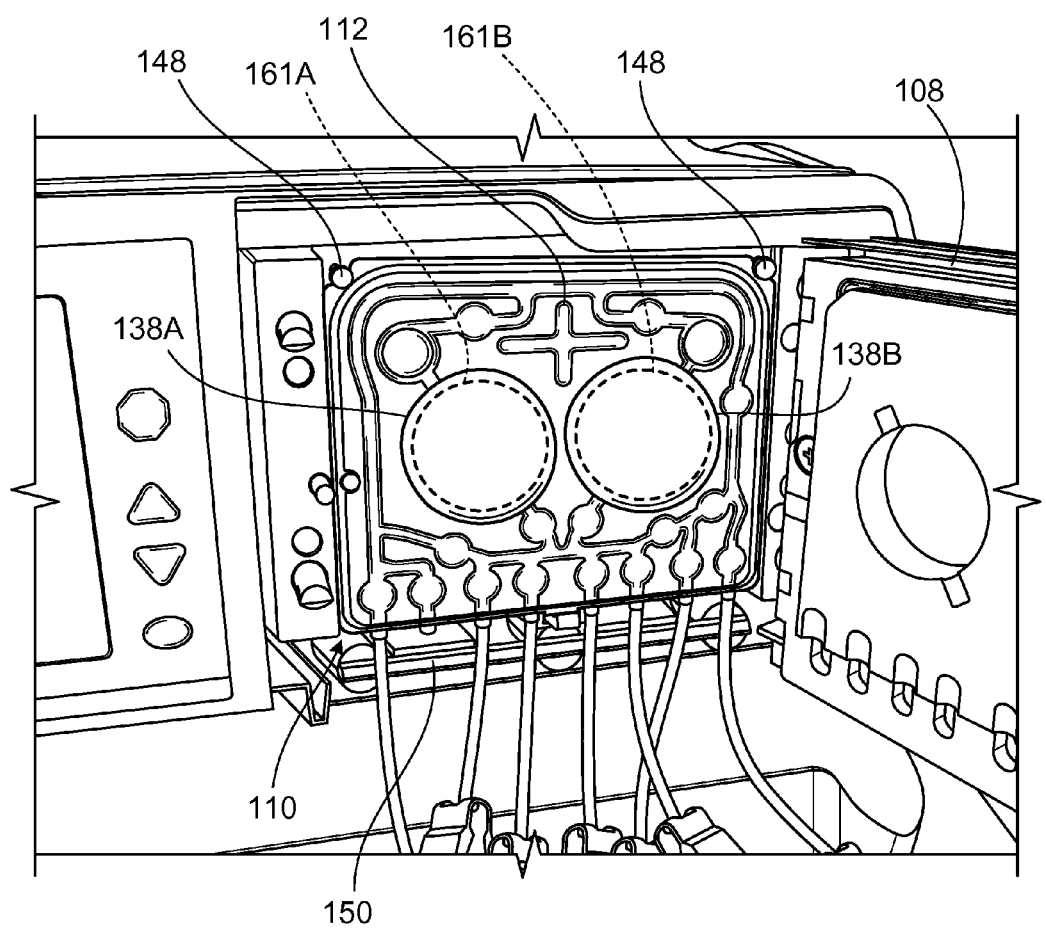
FIG. 10 is a partial perspective view of the PD cassette in the cassette compartment of the PD cycler of the PD system of FIG. 1.

As shown in FIG. 10, before treatment, the door 108 of the PD cycler 102 is opened to expose the cassette interface 110, and the cassette 112 is positioned with its membrane 140 adjacent to the cassette interface 110. The cassette 112 is positioned such that the pump chambers 138A, 138B of the cassette 112 are aligned with the actuators 133A, 133B. In order to ensure that the pump chambers 138A, 138B align with the actuators 133A, 133B, the cassette 112 is positioned between the locating pins 148 and the lower ledge 150 extending from the cassette interface 110. The asymmetrically positioned connectors 160 of the cassette act as keying features to reduce the likelihood that the cassette 112 will be installed with the membrane 140 facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108.

While loading the cassette 112 into the PD cycler 102, the actuators 133A, 133B are typically retracted completely into the actuator access ports 136A, 136B. This positioning of the actuators 133A, 133B can reduce the likelihood of damage to the actuators 133A, 133B during installation of the cassette 112. In addition, retracting the actuators 133A, 133B into the access ports 136A, 136B helps to prevent the actuators 133A, 133B from being prematurely coupled to the dome-shaped members 161A, 161B in the pump chambers 138A, 138B of the cassette 112 during insertion of the cassette 112 into the cassette enclosure 114. Such premature coupling of the actuators 133A, 133B to the dome-shaped members 161A, 161B could result in the actuators 133A, 133B being misaligned with the dome-shaped members 161A, 161B, which could lead to inaccurate fluid pumping.

Figure 11A:
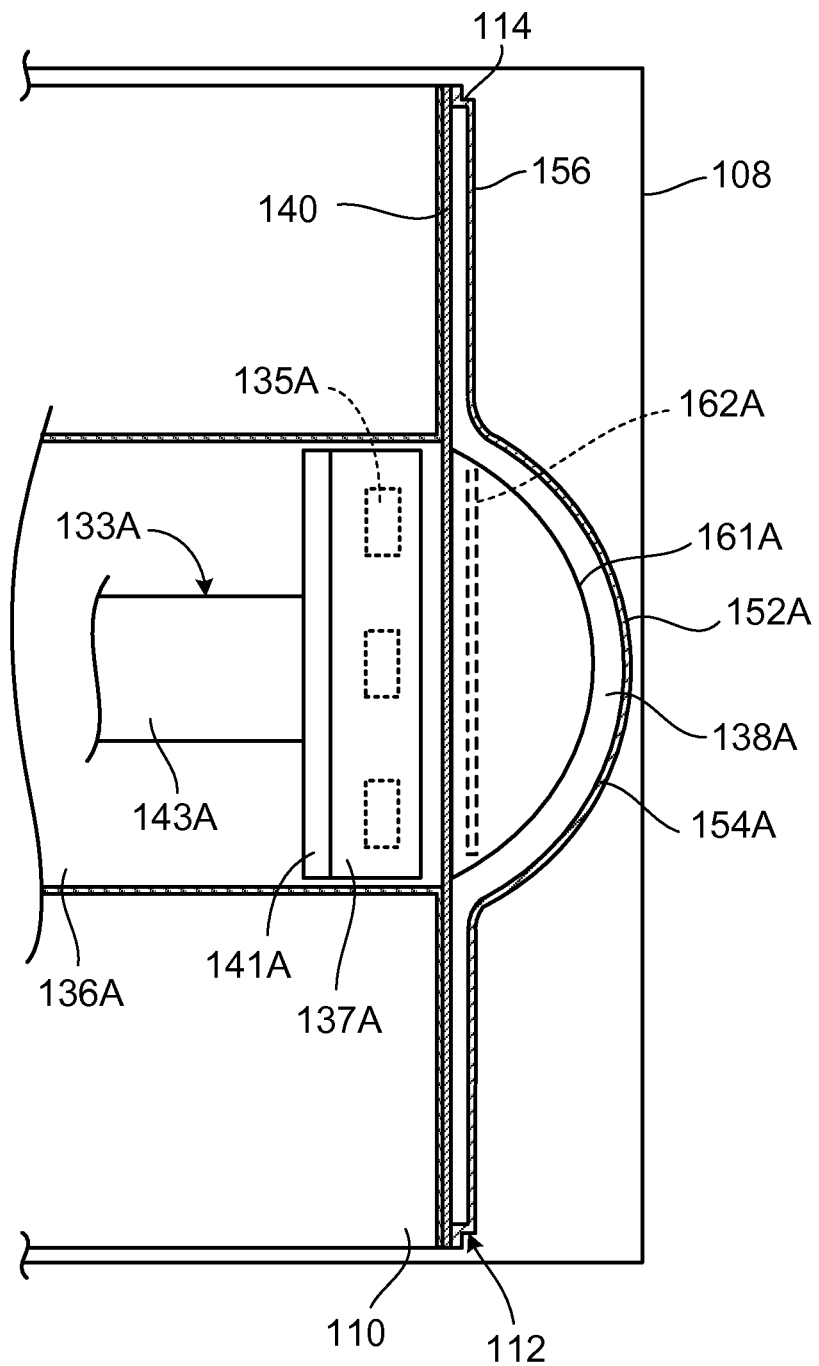
FIGS. 11A-11C are diagrammatic cross-sectional views of the PD cassette in the cassette compartment of the PD cycler of the PD system of FIG. 1, during different phases of operation.
Figure 11B:
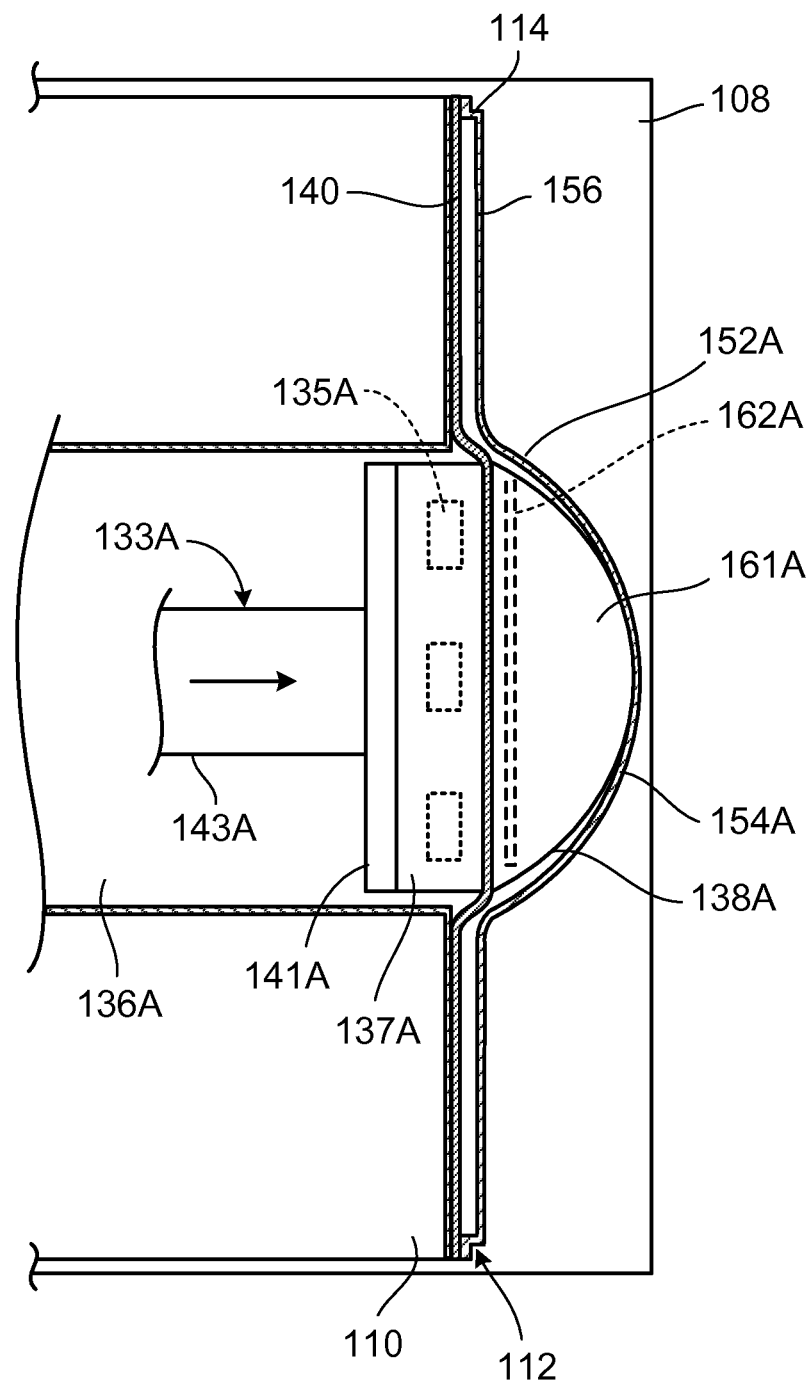
Figure 11C:
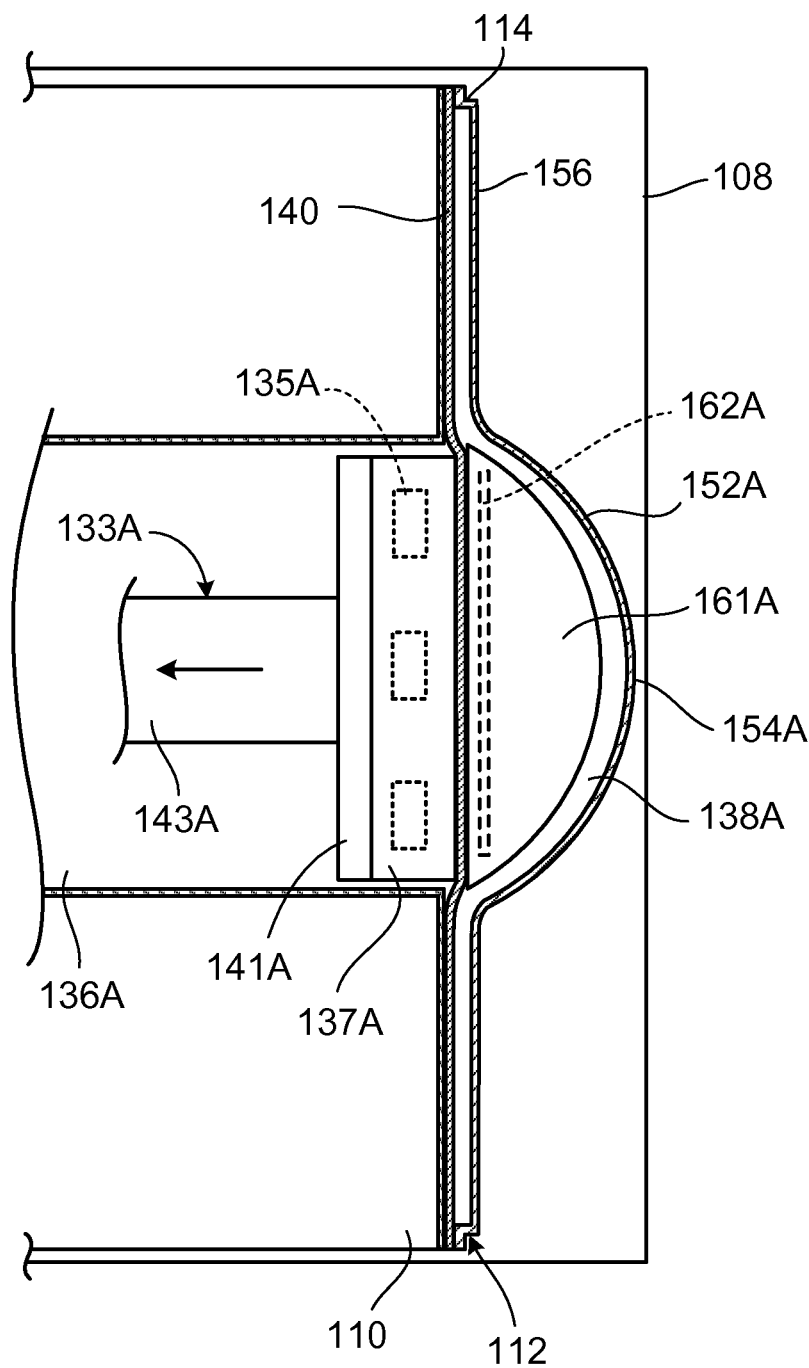

FIGS. 11A-11C illustrate the pump chamber 138A and its associated dome-shaped member 161A and actuator 133A throughout different phases of operation. The other dome-shaped member 161B and actuator 133B operate in a similar manner to pump dialysis solution to and from the other pump chamber 138B and thus, for simplicity, the operation of those components will not be separately described. Referring to FIG. 11A, with the cassette 112 positioned adjacent to the cassette interface 110, the door 108 is closed over the cassette 112 such that the cassette 112 is contained within the cassette compartment 114 between the door 108 and the cassette interface 110. An inflatable pad within the door 108 is then inflated to compress the cassette 112 between the door 108 and the cassette interface 110. This compression of the cassette 112 holds the projections 154A, 154B of the cassette 112 in the recesses 152A, 152B of the door 108 and presses the membrane 140 tightly against the raised ridges 165A, 165B, 167 extending from the planar surface of the rigid base 156 to form the enclosed fluid pathways 158, dome regions 146, and pump chambers 138A, 138B (shown in FIGS. 5 and 6).

As shown in FIG. 11B, after positioning the cassette 112 within the cassette compartment 114 and inflating the pad within the door 108, the actuator 133A is advanced toward the cassette 112 such that the magnetic actuator 133A becomes coupled to the magnetically attractive dome-shaped member 161A in the pump chamber 138A. Because the dome-shaped member 161A is attached to the membrane 140 in a manner such that the dome-shaped member 161A is centered within the pump chamber and because the cassette 112 is maintained in a desired position relative to the cassette interface 110 of the PD cycler 102, the actuator 133A is properly aligned with the dome-shaped member 161A as the actuator 133A is advanced. As a result, the actuator 133A and the dome-shaped member 161A become properly coupled by simply advancing the actuator 133A. After coupling the actuator 133A to the dome-shaped member 161A, the actuator is further advanced to deform the membrane 140 and force the dome-shaped member 161A toward the rigid base 156 of the cassette 112. As a result, the volume of the pump chamber 138A decreases, causing dialysis solution to be expelled from the pump chamber 138A via the fluid pathways 158 of the cassette 112 (shown in FIGS. 5-7).

After expelling the dialysis solution from the pump chamber 138A, the actuator 133A is again retracted, as shown in FIG. 11C. The magnetic coupling of the dome-shaped member 161A causes the dome-shaped member 161A to move the membrane 140 in the same direction as the retracting actuator 133A, thereby increasing the volume of the pump chamber 138A and generating vacuum pressure of about 150 mbar to about 200 mbar within the pump chamber 138A. As a result, dialysis solution is drawn into the pump chamber 138A of the cassette 112 via the fluid pathways 158 of the cassette 112 (shown in FIGS. 5-7).

While the magnet arrangement in the magnet plate 137A of the actuator 133A results in a low magnet field at distances of 1.5 inches or further from the magnet plate 137A, strong attraction forces (e.g., at least about 10 lbf, at least about 15 lbf, about 10 lbf to about 22 lbf) can be achieved between the actuator 133A and the magnetically attractive dome-shaped member 161A of the cassette 112 when the actuator 133A is brought into contact with the portion of the cassette membrane 140 adjacent the dome-shaped member 161A. It has been found that magnetic forces within this range are typically sufficient to draw fluid from the peritoneal cavity of a patient into the pump chamber 138A without causing the actuator 133A to become decoupled from the dome-shaped member 161A of the cassette 112 even when the patient is situated up to 36 inches below the PD cycler 102.

After drawing the dialysis solution into the pump chamber 138A, the dialysis solution can then be forced out of the pump chamber 138A by again returning the actuator 133A to the position shown in FIG. 11B, causing the membrane 140 and the dome-shaped member 161A to move toward the rigid base 156 and thus decreasing the volume of the pump chambers 138A, 138B.

During operation, with the cassette 112 secured within the compartment 114, the actuators 133A, 133B are reciprocated to sequentially alter the volume of each of the pump chambers 138A, 138B. Typically, as the actuator 133A is extended, the other actuator head 134B is retracted, and vice versa. As a result, dialysis solution is expelled from the pump chamber 138A at the same time that dialysis solution is drawn into the pump chamber 138B, and vice versa. As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the actuators 133A, 133B to reciprocate and selected inflatable members 142 are inflated to cause the spent dialysis solution to be drawn into the pump chambers 138A, 138B of the cassette 112 from the patient and then pumped from the pump chambers 138A, 138B to the drain via the drain line 132.

After draining the spent dialysis solution from the patient, heated dialysis solution is transferred from the heater bag 124 to the patient. To do this, the pump of the PD cycler 102 is activated to cause the actuators 133A, 133B to reciprocate and certain inflatable members 142 of the PD cycler 102 are inflated to cause the spent dialysis solution to be drawn into the pump chambers 138A, 138B of the cassette 112 from the heater bag 124 via the heater bag line 128 and then pumped from the pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the pump of the PD cycler 102 is activated to cause the actuators 133A, 133B to reciprocate and certain inflatable members 142 of the PD cycler 102 are inflated to cause the dialysis solution to be drawn into the pump chambers 138A, 138B of the cassette 112 from the selected dialysis solution bag 122 via its associated line 126 and then pumped from the pump chambers 138A, 138B to the heater bag 124 via the heater bag line 128.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations and a desired concentration for treatment is intermediate to the concentrations of the dialysis solution in two or more of the bags 122.

After completion of the PD treatment, the actuators 133A, 133B are retracted away from the cassette 112 to a sufficient distance to decouple the actuators 133A, 133B and the dome-shaped members 161A, 161B of the cassette 112. As the actuators 133A, 133B are retracted away from the cassette 112, the dome-shaped members 161A, 161B retract along with the actuators 133A, 133B and cause the membrane 140 to stretch. As the membrane 140 stretches, the resistance applied to the dome-shaped members 161A, 161B increases until eventually the resistive force applied to the dome-shaped members 161A, 161B by the membrane exceeds the attractive force between the actuators 133A, 133B and the dome-shaped members 161A, 161B, which causes the actuators 133A, 133B to become decoupled from the dome-shaped members 161A, 161B. The door 108 of the PD cycler 102 is then opened and the cassette 112 is removed from the cassette compartment 114 and discarded.

Because the PD system 100 does not require a vacuum system to move the portions of the membrane 140 overlying the pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective.

While certain implementations have been described, other implementations are possible.

While the magnets 135 of the actuators 133A, 133B have been described as being arranged in the roughly concentric circular pattern shown in FIG. 12, other magnet arrangements are possible. Examples of other magnet arrangements are illustrated in FIGS. 13-16. In each of FIGS. 13-16, the recesses 139A of the magnet plate 137A in which magnets 135 are disposed are shaded, and the recesses 139A that do not contain magnets are unshaded. As shown, in each of the illustrated magnet configurations, the positive poles of some of the magnets face outward and the positive poles of other magnets face inward. It has been found that this type of arrangement helps to reduce the magnetic field to which users of the PD cycler 102 are likely to be exposed. In particular, these magnet arrangements can result in a magnetic field of no more than about 10 Gauss (e.g., no more than about 5 Gauss) at a distance of about 1.5 inches from the actuator 133A, 133B while providing a magnetic force of at least about 10 lbf (e.g., at least about 15 lbf) with the dome-shaped member 161A coupled thereto.

In certain implementations, the actuators 133A, 133B can be easily disassembled and re-assembled. In such implementations, the magnet arrangements can be changed between uses to ensure that an optimal magnetic force is achieved between the actuators 133A, 133B and the dome-shaped members 161A, 161B.

While the dome-shaped member 161A has been described as including the film 175A bonded around the perimeter of the dome-shaped portion 173A to seal the magnetically attractive plate 162A between the film 175A and the dome-shaped portion 173A, in some implementations, the cassette membrane 140 itself is bonded to the perimeter region of the dome-shaped portion 173A in order to seal the magnetically attractive plate 162A between the membrane 140 and the dome-shaped portion 173A.

Figure 23:
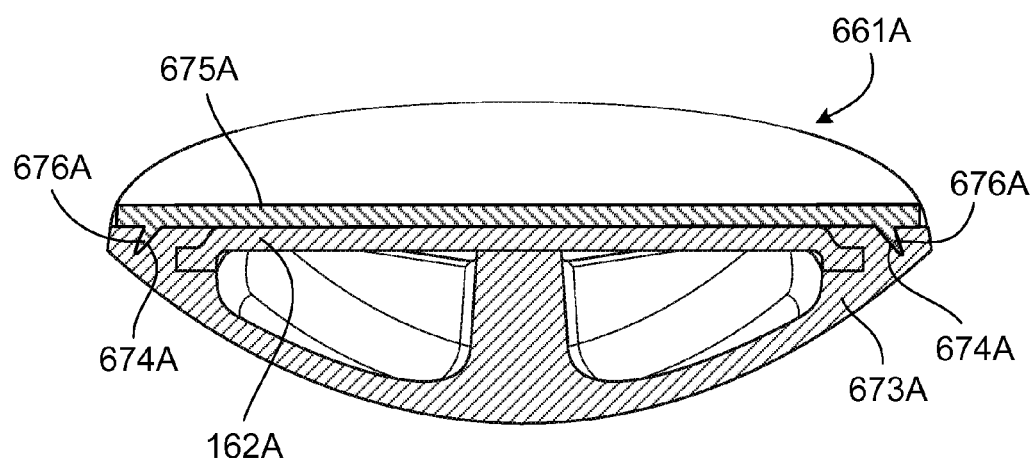
FIG. 23 is a perspective, cross-sectional view of another type of magnetically attractive dome-shaped member that can be used in the PD cassette of the PD system of FIG. 1.

While the dome-shaped member 161A has been described as including the film 175A bonded around the perimeter of the dome-shaped portion 173A to seal the magnetically attractive plate 162A between the film 175A and the dome-shaped portion 173A, a thicker and more rigid polymeric member can be used in place of the film 175A. As shown in FIG. 23, for example, a dome-shaped member 661A includes the magnetically attractive plate 162A sealed between a dome-shaped polypropylene portion 673A and a polypropylene cap 675A. The polypropylene cap 675A is thicker and more rigid than the film 175A and is, in many situations, more resistant than the film 175A to tearing or other damage that may jeopardize the biocompatible seal formed around the magnetically attractive plate 162A. Due to the thickness of the polypropylene cap 675A, it is typically impractical to use laser welds or certain other thermal bonds to secure the polypropylene cap 675A to the dome-shaped polypropylene portion 673A. Instead, barbs 676A extend from the polypropylene cap 675A and into mating recesses 674A in the dome-shaped polypropylene portion 673A to mechanically secure the polypropylene cap 675A to the dome-shaped polypropylene portion 673A.

To form the dome-shaped member 661A, the dome-shaped polypropylene member 673A is first injection molded. The magnetically attractive plate 162A is then disposed in a cavity formed in the dome-shaped polypropylene member 673A, and the assembly of the magnetically attractive plate 162A and the dome-shaped polypropylene member 673A is then inserted into a mold into which molten polypropylene is injected to overmold the polypropylene cap 675A. The injected molten polypropylene flows into the recesses 674A in the dome-shaped polypropylene portion 673A. As the molten polypropylene solidifies within those recesses 674A, the barbs 676A are formed. The barbs 676A mechanically connect the polypropylene cap 675A to the dome-shaped polypropylene portion 673A. In addition, the polypropylene of the cap 675A bonds with the polypropylene of the dome-shaped portion 673A to further secure the polypropylene cap 675A to the dome-shaped polypropylene portion 673A.

As an alternative to or in addition to using the barbs 674A to secure the polypropylene cap 675A to the dome-shaped polypropylene portion 673A, other securing arrangements can be used. In some implementations, for example, the mold into which the molten polypropylene is injected to form the polypropylene cap 675A is configured to include a gap between the outer perimeter of the dome-shaped polypropylene portion 673A and the inner surface of the mold.

As a result, the molten polypropylene, which will eventually solidify and form the cap, is allowed to flow around the outer perimeter of the dome-shaped portion 673A and solidify to form a wall that wraps around the circumferential edge of the dome-shaped polypropylene portion 673A and secures the cap to the dome-shaped portion 673A.

While the caps and the dome-shaped portions have been described as being formed of polypropylene, it should be understood that these components can be formed of any of the various biocompatible polymeric materials discussed above with respect to the dome-shaped portion 173A and the film 175A.

As an alternative to the techniques described above for forming the dome-shaped members 661A, other suitable techniques can be used. In certain implementations, the dome-shaped member is formed using an insert injection molding technique. In such implementations, a two-part mold is opened and a steel plate is positioned between the two mold parts. The mold parts are then brought together to form a dome-shaped cavity in which the steel plate is positioned. Next, molten biocompatible resin is injected into the cavity so that the steel plate becomes encapsulated within the molten resin. After the resin has cooled, the mold parts are again pulled apart and the dome-shaped member is removed.

As an alternative to or in addition to injection molding, other techniques, such as machining techniques, can be used to form the dome-shaped members 161A, 661A. In certain implementations, the polymeric portions 173A, 175A, 673A, 675A and the magnetic plate 162A are all separately made and then attached (e.g., thermally or adhesively bonded or mechanically assembled) to one another to form the dome-shaped members 161A, 661A.

Figure 24:
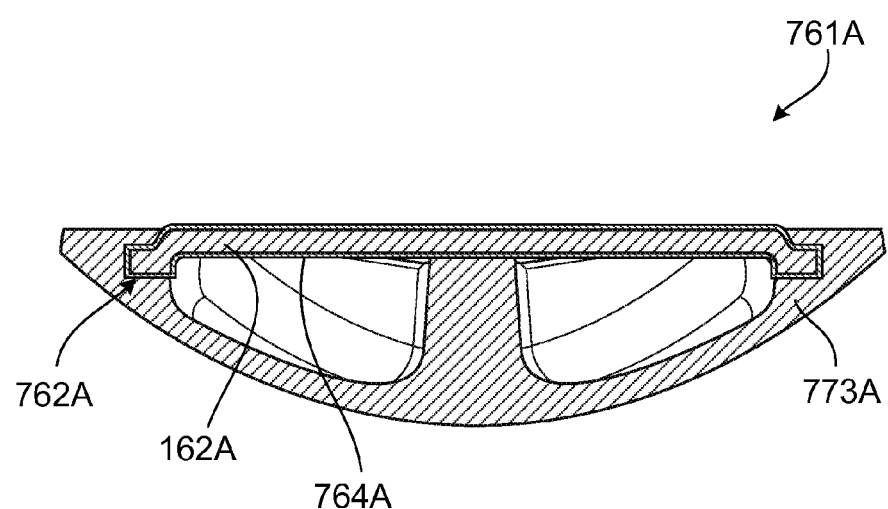
FIG. 24 is a perspective, cross-sectional view of a further type of magnetically attractive dome-shaped member that can be used in the PD cassette of the PD system of FIG. 1.

While the plates 162A, 162B of the dome-shaped members 161A, 161B have been described as being sealed between resin portions of the dome-shaped members, other constructions can be used. In certain implementations, for example, the magnetically attractive plate is coated with a biocompatible material, such as polytetrafluoroehtylene (PTFE), and the coated plate itself forms the rear surface of the dome-shaped members. As shown in FIG. 24, for example, a dome-shaped member 761A includes a PTFE-coated steel plate 762A that is secured to dome-shaped portion 773A. The PTFE-coated steel plate 762A simply includes the steel plate 162A described above with a PTFE coating 764A that encapsulates the plate 162A. To make the dome-shaped member 761A, the steel plate 162A is first coated with PTFE to form the coated plate 762A. A pre-form of the dome-shaped portion 773A is then injection molded. The coated plate 762A is then placed within a recessed region of the pre-form of the dome-shaped portion 773A, and the assembly of the coated plate 762A and the pre-form are disposed in a mold into which molten polypropylene is injected. The molten polypropylene covers the circumferential region of the coated plate 762A and solidifies to encapsulate the circumferential region of the coated plate 762A within polypropylene and thereby form the remainder of the dome-shaped polypropylene portion 773A. A central portion of the rear surface of the coated plate 762A remains exposed.

While the coating of the coated plate 762A has been described as being formed of PTFE, other types of coatings can alternatively or additionally be used. In certain implementations, for example, the coating is formed of gold or Parylene. Similarly, while the plate has been described as being formed of steel and the dome-shaped portion 763A has been described as being formed polypropylene, those components can alternatively be formed of any of the various other materials described above with respect to the corresponding components in the dome-shaped members 161A and 661A.

Figure 17:
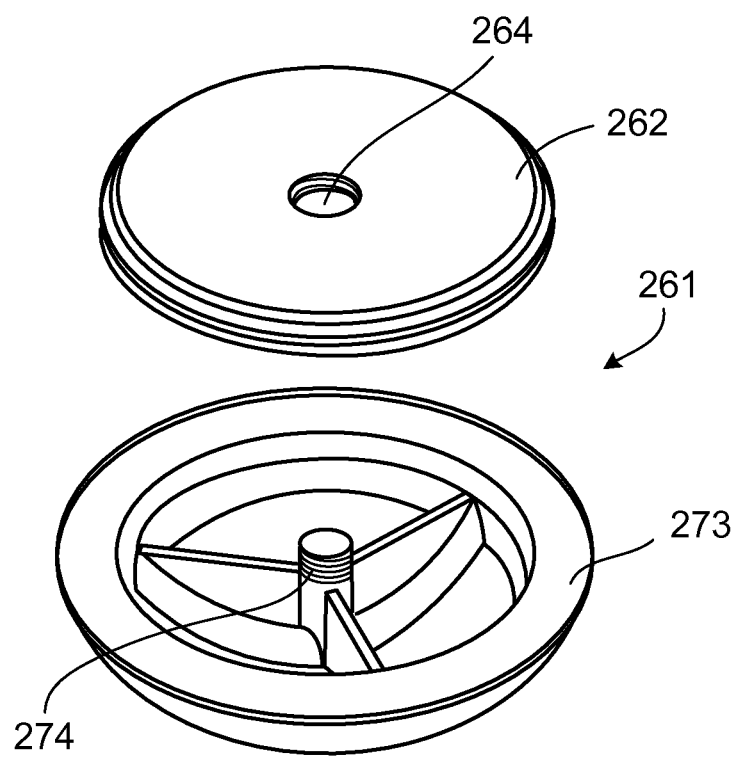
FIG. 17 is an exploded perspective view of an alternative magnetically attractive dome-shaped member that includes an exposed magnetic plate and can be used in the PD cassette of the PD system of FIG. 1.

Dome shaped members having other constructions can also be used. FIG. 17, for example, illustrates an exploded perspective view of an alternative dome-shaped member 261, which includes a biocompatible, magnetically attractive plate 262 secured to a dome-shaped biocompatible, polymeric member 273. The plate 262 includes a threaded bore 264 that can matingly engage threads of a threaded stem 274 extending from the dome-shaped polymeric member 273 to secure the plate 262 and the dome-shaped member 273 together. Because the plate 262 is not encapsulated, it may be exposed to fluid within the pump chamber of the cassette that is to be delivered to a patient. Thus, the plate 262 is formed of a biocompatible material. In certain implementations, for example, the plate 262 is formed of stainless steel, such as stainless steel 417, stainless steel 410, or stainless steel 17-4. As an alternative to stainless steel, other types of magnetically attractive, biocompatible materials can be used to form the plate 262 of the dome-shaped member 261. The plate 262 can, for example, include a steel plate or magnet that is coated with a biocompatible material, such as PTFE, gold, or Parylene.

As an alternative to forming the entire plate 262 of a magnetically attractive, biocompatible material, a biocompatible coating can be applied over a non-biocompatible magnetically attractive material, such as steel.

While the plate 262 has been described as being secured to the dome-shaped member by a threaded connection, other types of connections, such as thermal or adhesive bonding, can alternatively or additionally be used.

While the dome-shaped member 273 has been described as being formed of a biocompatible polymeric material, biocompatible materials of other types, such as biocompatible metals, can alternatively or additionally be used. In certain implementations, for example, both the magnetic plate 262 and the dome-shaped member 273 are formed of stainless steel.

While the pump chambers 138A, 138B have been described as being sized to pump about 12-13 ml of fluid with each actuator stroke, the pump chambers 138A, 138B and the dome-shaped members 161A, 161B disposed in those chambers can be sized to pump different volumes of fluid. In certain implementations, for example, the pump chambers 138A, 138B are sized to pump about 25-30 ml of fluid per actuator stroke.

While the dome-shaped members 161A, 161B have been described as being attached to the inner surface of the cassette membrane 140, in certain implementations, the cassette includes members that are not attached to the cassette membrane 140. In certain implementations, for example, the dome-shaped members are provided with magnets that are attracted to the magnets of the actuators. As a result of the strong attraction between these magnets, the magnets can help to properly align the dome-shaped members within the pump chambers. During shipping of cassettes including these types of dome-shaped members, it is particularly advantageous to use the cover 177 described above with respect to FIG. 9 in order to reduce the risk of damage to those members.

Figure 18:
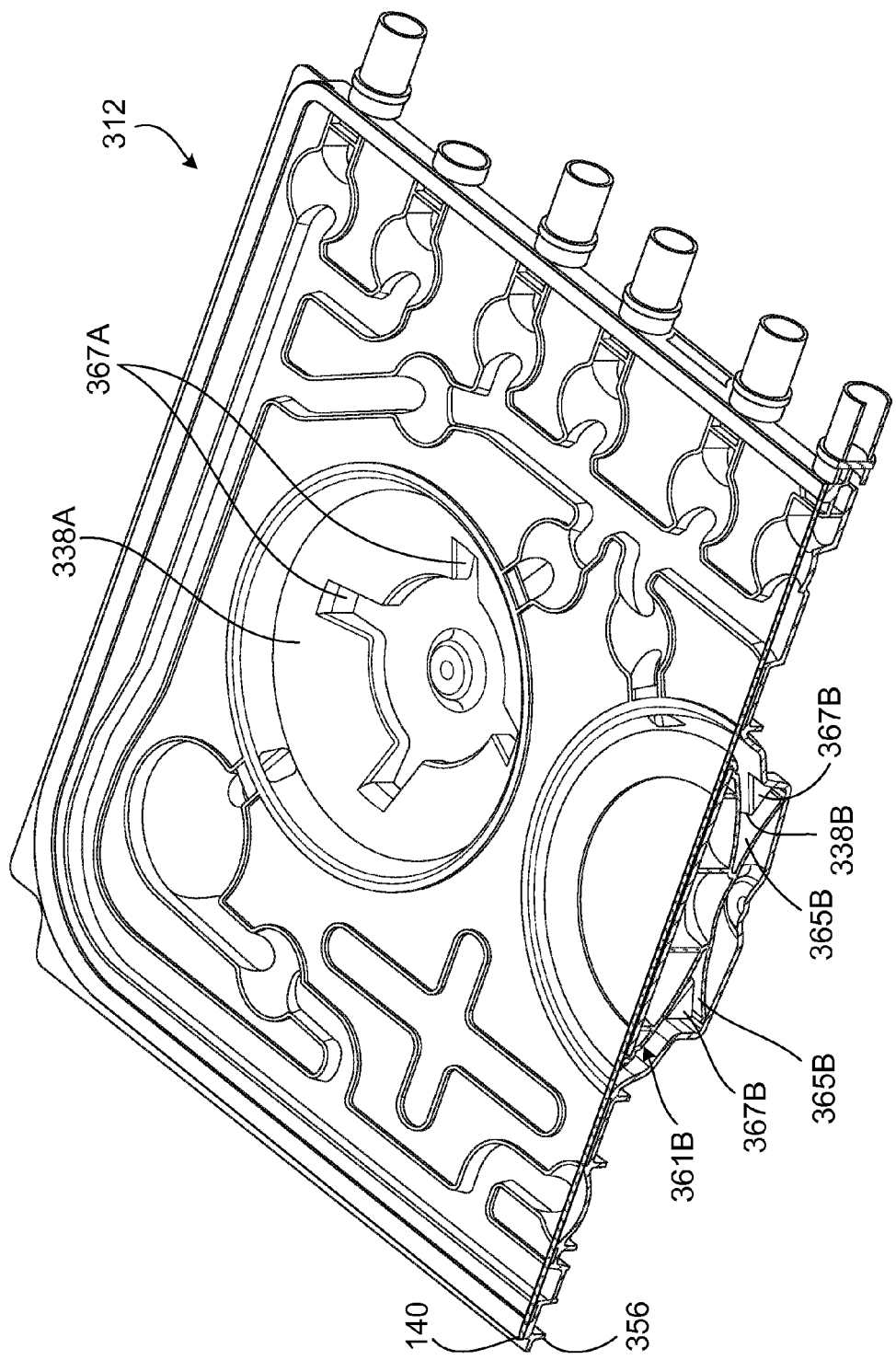
FIG. 18 is a perspective, cross-sectional view of an alternative PD cassette that includes a magnetically attractive dome-shaped member disposed in a fluid pump chamber of the PD cassette where the member includes feet that engage slots formed in a base of the PD cassette to hold the member in a central portion of the fluid pump chamber.
Figure 19:
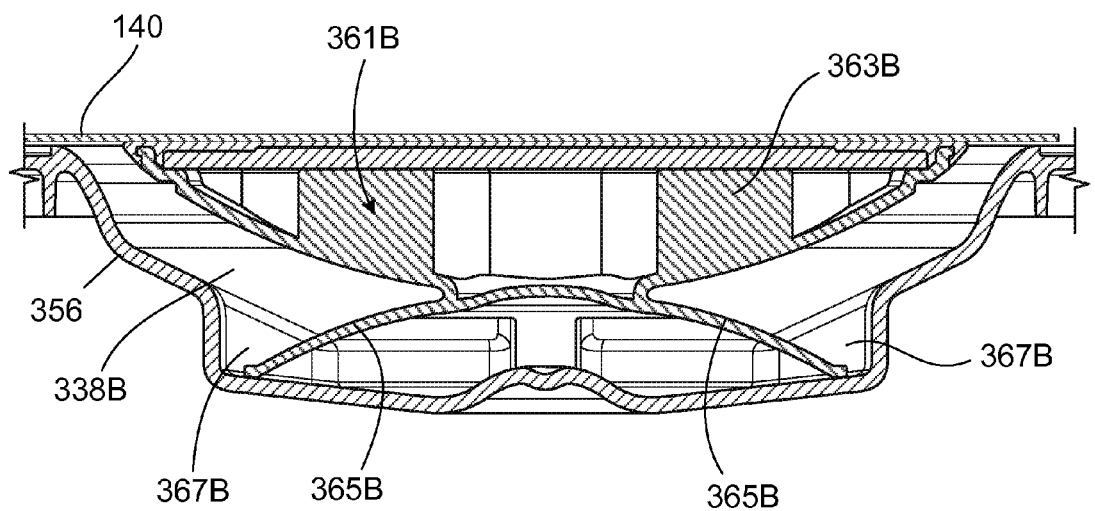
FIG. 19 is a cross-sectional view of the fluid pump chamber of the PD cassette of FIG. 18.

In other implementations, as shown in FIGS. 18 and 19, a PD cassette 312 includes a magnetically attractive member 361B that is mechanically restrained within a pump chamber 338B formed between a rigid base 356 and the membrane 140 to maintain proper alignment of the member 361B within the pump chamber 338B. A magnetically attractive member 361A that is identical to the member 361B is typically positioned in an additional pump chamber 338A formed between the rigid base 356 and the membrane 140. The member 361A is not shown in the pump chamber 338A in FIG. 18 in order to provide a clearer view of the portion of the rigid base 356 that forms the pump chamber 338A, which is similar to the portion of the rigid base 356 that forms the pump chamber 338B. As shown in FIGS. 18 and 19, the magnetically attractive member 361B includes a dome-shaped portion 363B that is similar in construction to the dome-shaped member 161A described above. Four resilient legs 365B extend from the dome-shaped portion 363B and sit within slots 367B formed by the base 356. The top surface of the member 361B is in contact with or in near contact with the membrane 140 when the member 361B is in an uncompressed state. As a result, the resilient legs 365B are retained in the slots 367B of the base 356. The engagement of the legs 365B with the portions of the base 356 forming the slots 367B inhibits rotational and radial movement of the member 361B relative to the base 356 and thus keeps the member 361B positioned within a central region of the pump chamber 338B.

The cassette 312 can be used in the PD cycler 102 in generally the same way as the cassettes described above. As the actuator 133B is advanced toward the base 356 of the cassette 312, the resilient legs 367B of the member 361B collapse and allow the hemispherical portion 363B of the member 361B to come into contact with or into near contact with the base 356. The resilient legs 367B can, for example, collapse upon being subjected to a compression force of about two pounds or greater (e.g., about five pounds or greater). The volume of the pump chamber 338B decreases as a result of this movement, causing fluid to be expelled from the pump chamber 338B. The actuator 133B is subsequently retracted, and the magnetic coupling between the actuator 133B and the magnetically attractive plate within the hemispherical portion 363B of the member 361 causes the member 361B to be refracted along with the actuator 133B. The volume of the pump chamber 338B increases as a result of this movement, causing fluid to be drawn into the pump chamber 338B.

Figure 20A:
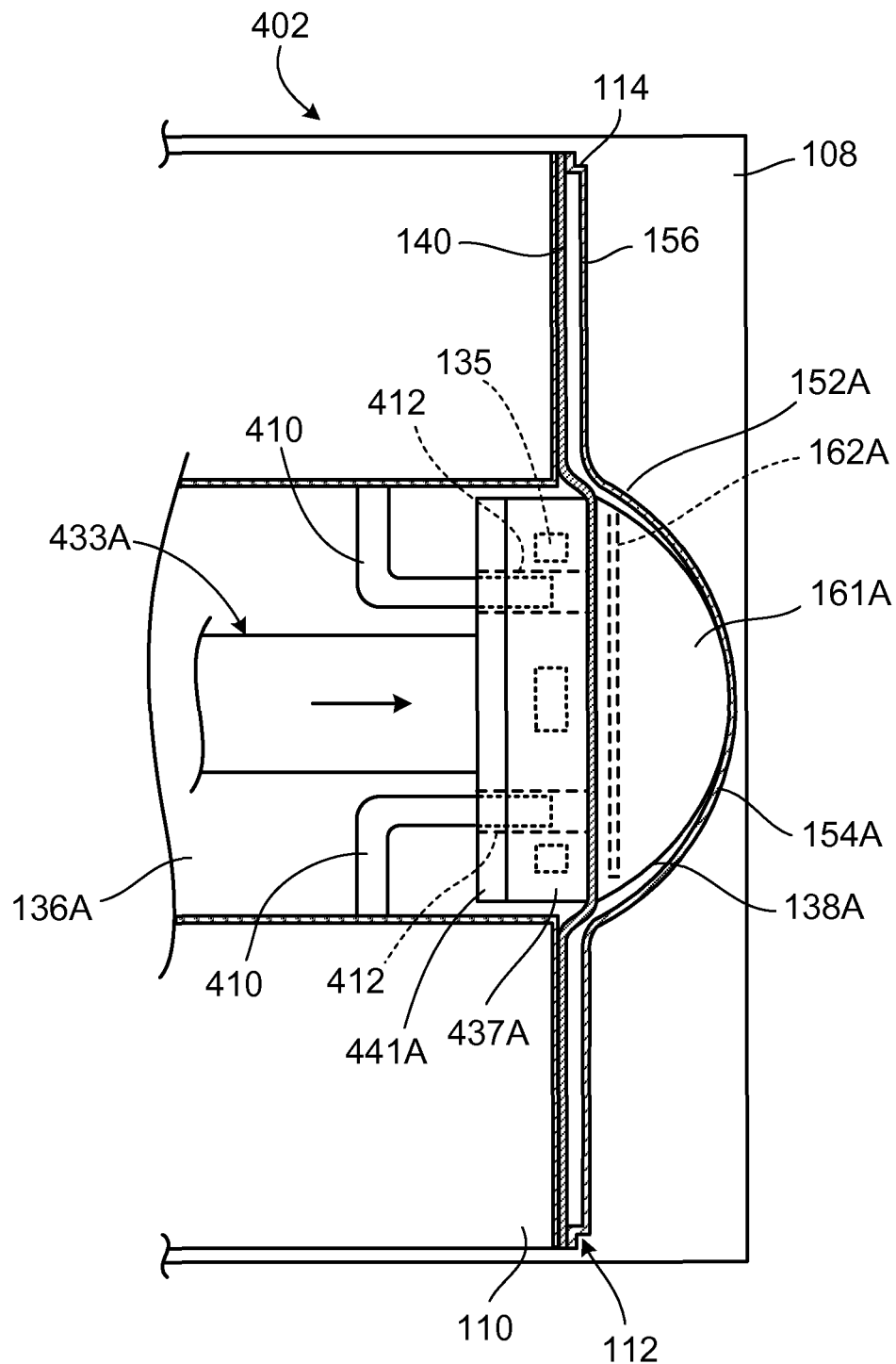
FIGS. 20A and 20B are diagrammatic cross-sectional views of a PD cycler that includes decoupling posts, during and after treatment, respectively.
Figure 20B:
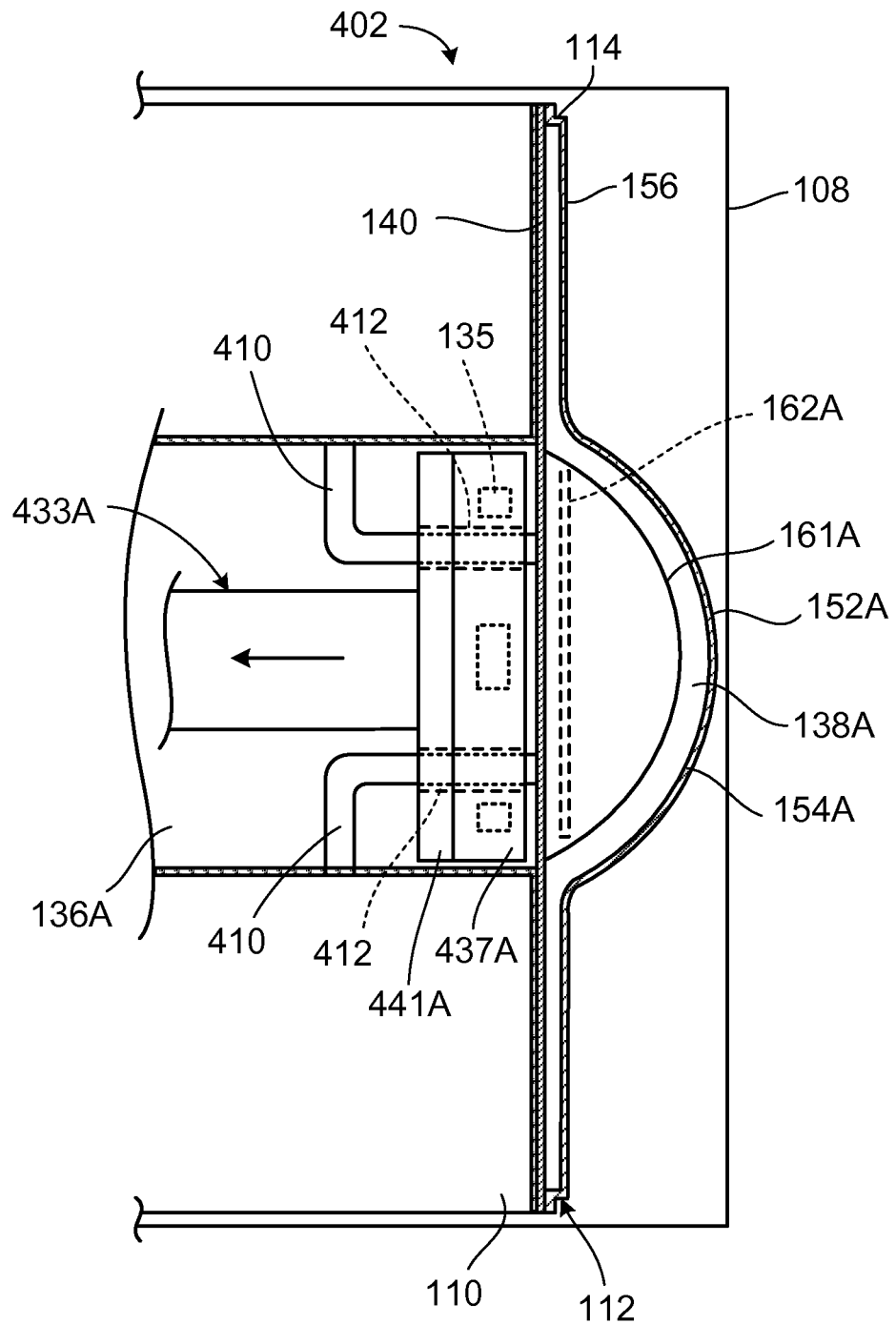

While the actuators 133A, 133B have been described as being decoupled from the magnetically attractive members 161A, 161B; 261A, 261B; 361A, 361B by retracting the actuators 133A, 133B until the resistance of the cassette membrane 140 exceeds the coupling force between the actuators 133A, 133B and those members, other techniques can be used. For example, FIGS. 20A and 20B show the operation of a PD cycler 402 that includes decoupling posts 410 and an actuator 433A that has bores 412 that extend through a magnet plate 437A and cap plate 441A of the actuator 433A. The bores 412 are sized and arranged to receive the decoupling posts 410 of the PD cycler 402. Apart from the decoupling posts 410 and the bores 412 in the actuator 433A, the PD cycler 402 is substantially the same as the PD cycler 102 described above. As with the PD cycler 102 described above, the PD cycler 402 also includes a second actuator that is similar to the actuator 433A. During use, the cassette 112 is disposed within a cassette enclosure 414 of the PD cycler 402 such that the actuators of the PD cycler 402 align with the pump chambers 138A, 138B of the cassette. For simplicity, only the operation of the actuator 433A associated with the pump chamber 138A is shown and described with respect to FIGS. 20A and 20B.

The PD cycler 402 is generally operated in the same manner as the PD cycler 102 described above. As shown in FIG. 20A, as the actuator 433A is advanced to expel fluid from the pump chamber 138A, the membrane 140 of the cassette 112 is not in contact with the decoupling posts 410. Rather, the decoupling posts 410 terminate at points within the bores 412 of the actuator 433A. As the actuator 433A is reciprocated during use to draw fluid into and pump fluid out of the pump chamber 138A, the decoupling posts 410 remain out of contact with the membrane 140. Thus, fluid can be expelled from and drawn into the pump chamber 138A without interference from the decoupling posts 410.

Upon completion of the treatment, the actuator 433A is retracted into the actuator access port 136A. The decoupling posts 410 are held in a fixed position. As a result, as the actuator 433A, the membrane 140, and the dome-shaped member 161A are together retracted, the ends of the decoupling posts 410 contact the membrane 140 and resist further axial movement of the membrane 140 and the dome-shaped member 161A. Due to the bores 412 formed in the actuator 433A, the actuator 433A is able to be drawn proximal to the ends of the decoupling posts 410. Continued retraction of the actuator 433A causes the dome-shaped member 161A to become decoupled from the magnets 135 of the actuator 433A, as shown in FIG. 21B. The decoupling posts 410 advantageously allow the actuator 433A and the dome-shaped member 161A to be decoupled from one another without excessively stretching the membrane 140 of the cassette 112.

While the magnetically attractive members and the pump chambers of the above-described cassettes have been described as being dome-shaped, magnetically attractive members and pump chambers of other mating shapes can be used. For example, the magnetically attractive members and pump chambers can be cylindrical, rectangular, etc.

While some of the magnetically attractive members that are disposed within the cassette pump chambers have been described as including one or more biocompatible polymers, they can alternatively be formed of other types of biocompatible materials, such as biocompatible metals. In some implementations, for example, the dome-shaped members are formed entirely of stainless steel.

While the actuators of the PD cyclers described above include permanent magnets, other types of magnetic devices can be used. In certain implementations, for example, the actuators are equipped with electromagnetic devices. In such implementations, the magnetic coupling between the actuators and the members disposed within the pump chambers of the cassette can be broken by simply turning off the current to the electromagnetic device.

While the magnets 135 have been described as being contained in the actuators of the PD cycler and the members disposed within the pump chambers of the cassettes have been described as including magnetically attractive materials that can be attracted to the magnets in the actuators, in some implementations, the members disposed within the pump chambers contain the magnets and the actuators include the magnetically attractive materials that can be attracted to the magnets. In still other implementations, both the member disposed within the pump chambers and the actuators of the PD cycler contain magnets.

Figure 21:
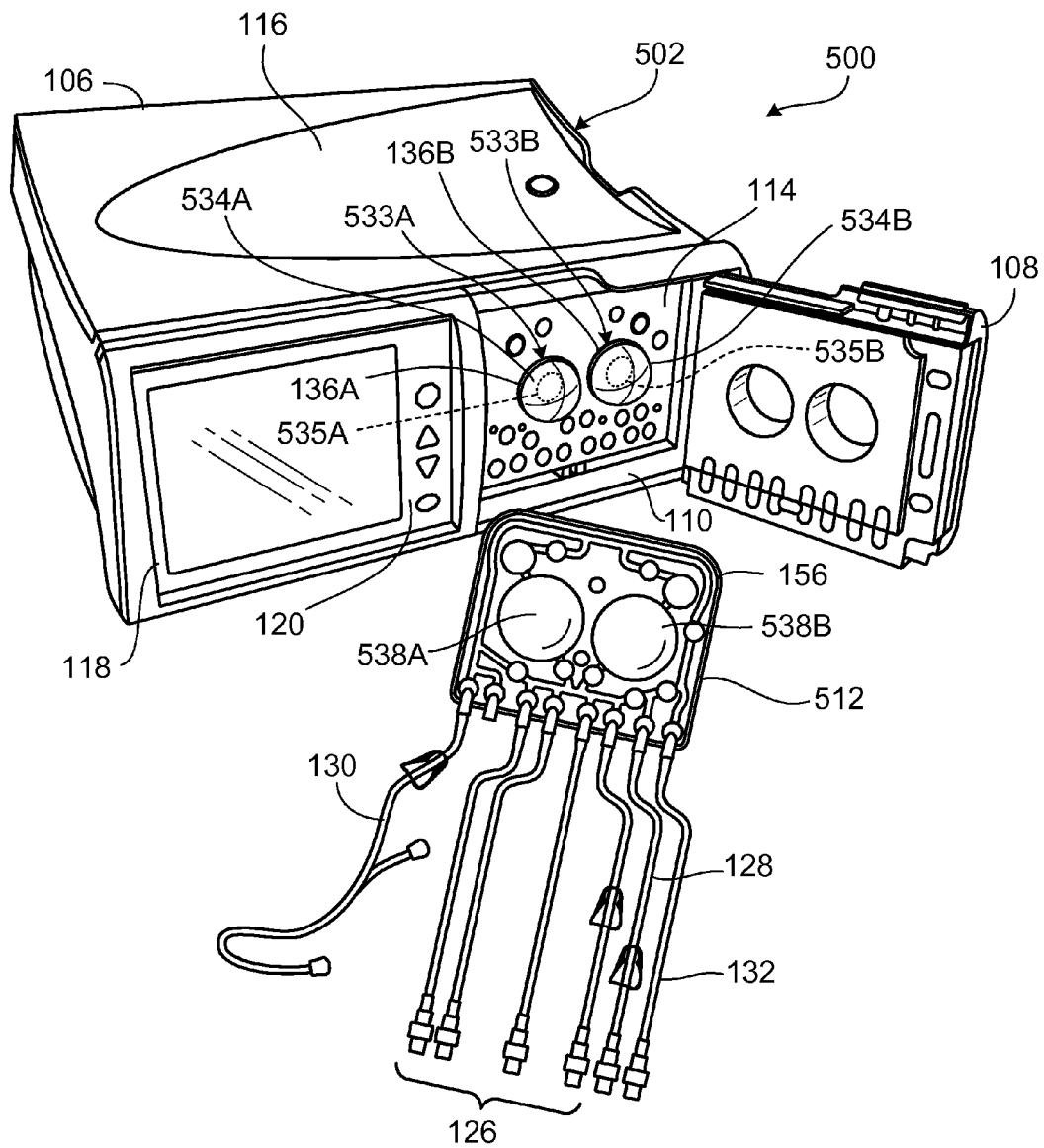
FIG. 21 is a perspective view of a PD cycler and PD cassette of another PD system. A door of the PD cycler is shown in the open position to expose magnetic, dome-shaped piston heads of the PD cycler that can be coupled to a magnetically attractive membrane of the PD cassette during use.

While the dialysis systems described above include magnetic actuators that are coupled during use to magnetically attractive members disposed within pump chambers of a cassette, in certain implementations, a dialysis system includes a dialysis machine having magnetic actuators that are magnetically coupled directly to a magnetically attractive membrane that partially forms the pump chambers of the cassette. As shown in FIG. 21, for example, a PD system 500 includes a PD cycler 502 having pistons (also referred to as actuators) 533A, 533B that include electromagnetic, dome-shaped piston heads 534A, 534B attached (e.g., engaged by mating threads, thermally bonded, adhesively bonded, snap fit, etc.) to piston shafts 543A, 543B. Each of the piston heads 534A, 534B includes a cavity in which an electromagnet is contained. Each of the piston heads 534A, 534B can, for example, include a rear end cap that can be secured to the front dome-shaped portion of the piston head to form the cavity in which the electromagnet is contained. Alternatively, the electromagnet can be threadedly engaged with or otherwise attached to the front dome-shaped member of the piston head.

A power source (e.g., a battery or a mains power supply to which the PD cycler 502 is connected) can be connected to the electromagnets in the piston heads 534A, 534B via lead lines such that current can be transmitted to the electromagnets. When no current is supplied to the electromagnet, the magnetic field surrounding the piston heads 534A, 534B is very weak such that little or no attraction is experienced between the piston heads 534A, 534B and magnetically attractive objects in close proximity to the piston heads 534A, 534B. A current flowing in a first direction through the electromagnet creates a magnetic field causing magnets in close proximity to the piston heads 534A, 534B to be attracted to the piston heads 534A, 534B, and a current flowing in a second, opposite direction through the piston heads 534A, 534B creates a magnetic field causing magnets (of the same polarity as the magnets mentioned above) in close proximity to the piston heads 534A, 534B to be repelled away from the piston heads 534A, 534B.

The piston heads 534A, 534B are typically formed of stainless steel. However, other metals, such as aluminum, and certain polymeric materials can alternatively or additionally be used to the form the piston heads 534A, 534B.

An example of a suitable electromagnet is the EM050-12-222 electromagnet, available from APW Company (Rockaway, N.J.). However, other types of electromagnets can alternatively or additionally be used.

Each of the pistons 533A, 533B is connected to a motor (e.g., a stepper motor) positioned in the housing 106 of the PD cycler 502 so that the pistons 533A, 533B can be axially moved within the access ports 136A, 136B formed in the cassette interface 110 of the PD cycler 502. Apart from the electromagnetic piston assemblies of the PD cycler 502, the PD cycler 502 has generally the same structure as and operates in a similar manner to the PD cycler 102 described above.

The PD system illustrated in FIG. 21 also includes a PD cassette 512 that includes a magnetically attractive membrane 540 (shown in FIGS. 22A-22C) attached to the base 156 of the cassette 512. Similar to the membrane 140 described above, the magnetically attractive membrane 540 covers substantially the entire base 156 and is attached (e.g., thermally or adhesively bonded) only to the periphery of the base 156. The magnetically attractive membrane 540 is typically formed of the same materials as the membrane 140 but also includes an outer layer of magnetically attractive material. The outer layer can, for example, be a layer of magnetically attractive paint. The outer layer is typically restricted only to those portions of the membrane overlying the fluid pump chambers 538A, 538B. However, the outer layer of magnetically attractive material can alternatively be applied to the entire surface of the membrane. One example of a suitable magnetically attractive paint is RUST-OLEUM® Specialty magnetic latex primer, available from RUST-OLEUM® Corporation (Vernon Hills, Ill.).

Unlike the PD cassette 112 described above, the PD cassette 512 does not include magnetically attractive dome-shaped members inside its pump chambers 538A, 538B. Instead, the pump chambers 538A, 538B are vacant, except for containing liquid during use. As described in greater detail below, when the electromagnetic piston heads 534A, 534B are magnetically activated, they can be coupled directly to the magnetically attractive membrane 540 of the cassette 512 such that the magnetically attractive membrane 540 can be reciprocated along with the piston heads 534A, 534B.

In order to begin treatment, the cassette 512 is loaded into the cassette compartment 114 of the PD cycler 502 in much the same way that the cassette 112 was previously described as being loaded into the cassette compartment 114 of the PD cycler 102. While loading the cassette 512 into the PD cycler 502, current does not flow through the electromagnets 535A, 535B of the pistons 533A, 533B such that little or no magnetic attraction is experienced between the magnetic piston heads 534A, 534B and the magnetically attractive membrane 540 of the cassette 512. In addition, the pistons 533A, 533B are typically retracted completely into the access ports 136A, 136B to reduce the likelihood of damage to the membrane 540 during installation of the cassette 512. Retracting the pistons 533A, 533B into the access ports 136A, 136B can also help to prevent the piston heads 534A, 534B from being prematurely coupled to the magnetically attractive membrane 540 during installation, which could result in the piston heads 534A, 534B being misaligned with respect to the pump chambers 538A, 538B and could lead to inaccurate fluid pumping.

Figure 22A:
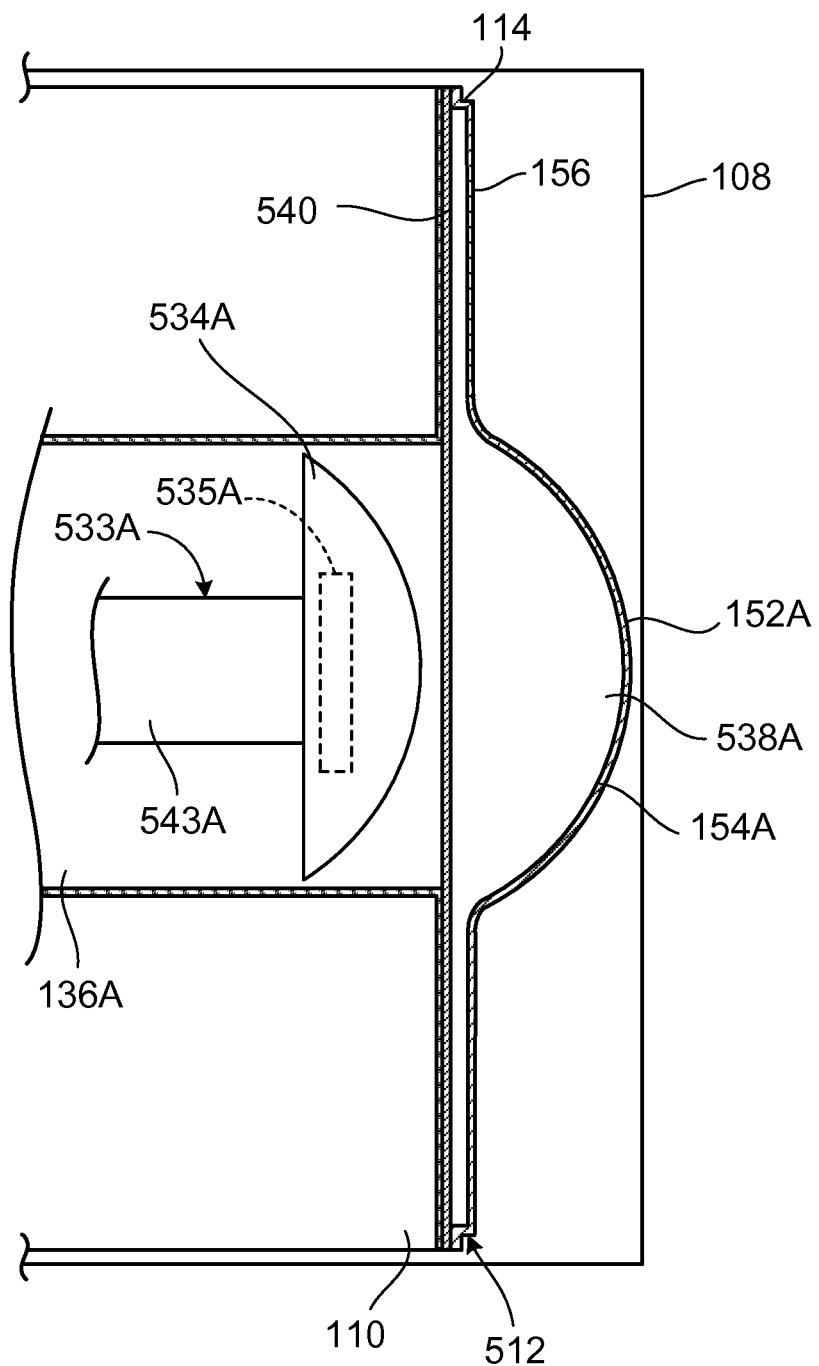
FIGS. 22A-22C are diagrammatic cross-sectional views of the PD cassette in the cassette compartment of the PD cycler of the PD system of FIG. 21, during different phases of operation.
Figure 22B:
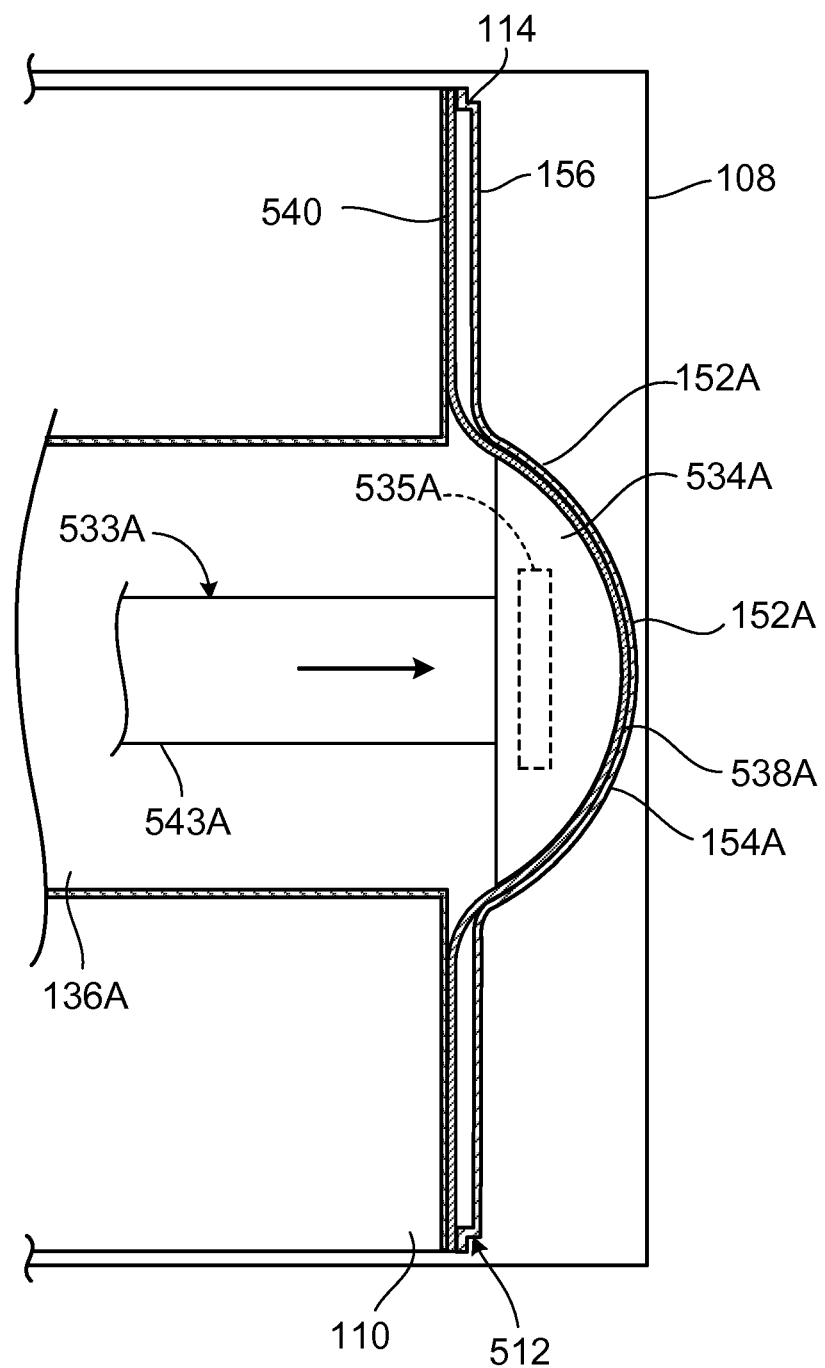
Figure 22C:
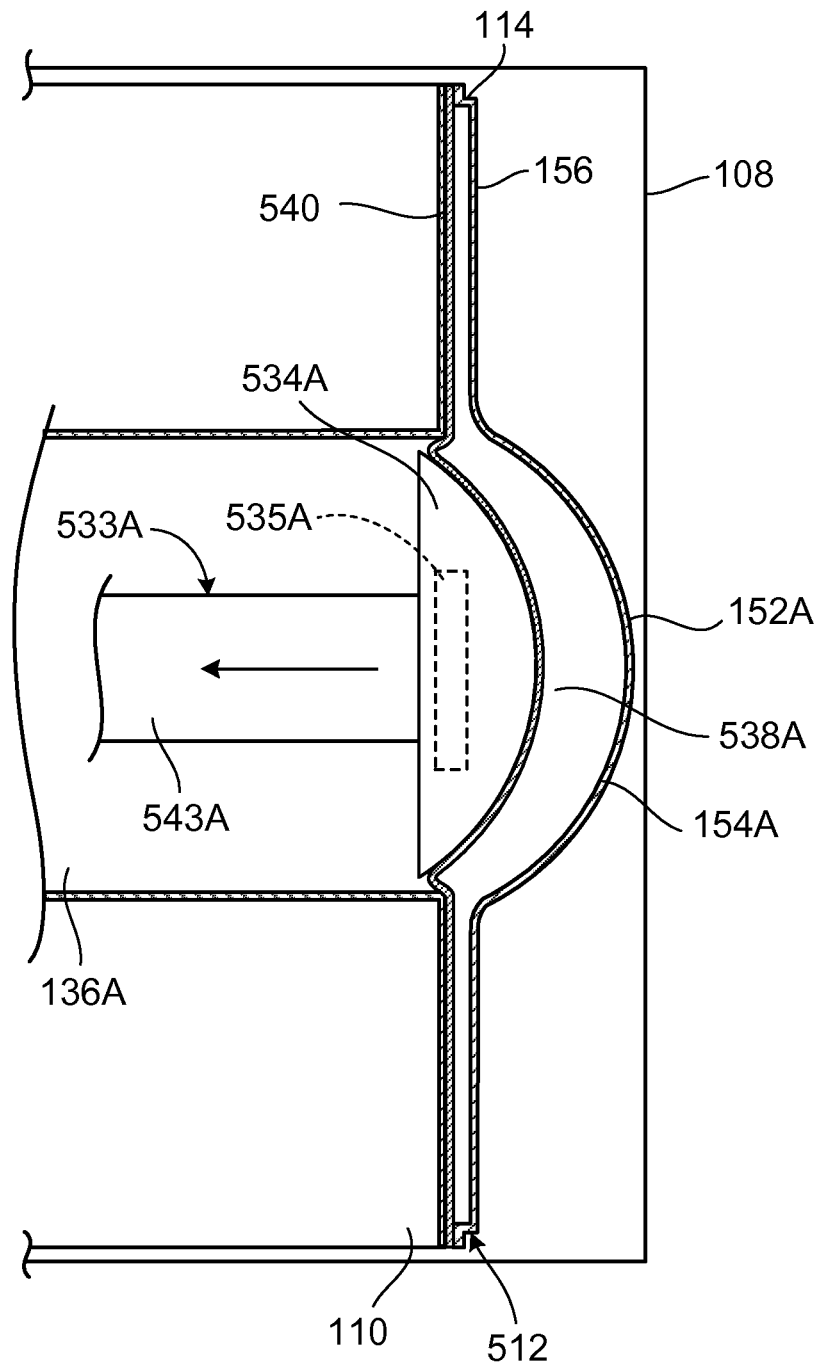

FIGS. 22A-22C illustrate the portion of the cassette 512 including the pump chamber 538A and its associated piston 533A throughout different phases of operation. The other piston 533B and pump chamber 538B cooperate in a similar manner to pump dialysis solution to and from the other pump chamber 538B and thus, for simplicity, the operation of those components will not be separately described. Referring to FIG. 22A, with the cassette 512 positioned adjacent to the cassette interface 110, the door 108 of the PD cycler 502 is closed over the cassette 512 such that the cassette 512 is contained within the cassette compartment 114 between the door 108 and the cassette interface 110. An inflatable pad within the door 108 is then inflated to compress the cassette 512 between the door 108 and the cassette interface 110. This compression of the cassette 512 holds the projections 154A, 154B of the cassette 512 in the recesses 152A, 152B of the door 108 and presses the membrane 540 tightly against the raised ridges extending from the planar surface of the rigid base 156 to form the various fluid pathways and chambers of the cassette 512.

As shown in FIG. 22B, after positioning the cassette 512 within the cassette compartment 114, a current is applied to the piston head 534A to magnetically activate the piston head 534A, and the piston 533A is advanced toward the cassette 512 such that the piston head 534A becomes coupled to the portion of the magnetically attractive membrane 540 overlying the pump chamber 538A of the cassette 512. The piston 533A is then further advanced to deform the membrane 540 toward the rigid base 156 of the cassette 512, causing dialysis solution to be expelled from the pump chamber 538A via the fluid pathways of the cassette 512.

After expelling the dialysis solution from the pump chamber 538A, the piston 533A is again retracted, as shown in FIG. 22C. Due to the magnetic coupling between the piston head 534A and the membrane 540, the membrane 540 is retracted along with the piston 533A, thereby increasing the volume of the pump chamber 538A and generating vacuum pressure of about 150 mbar to about 200 mbar within the pump chamber 538A. As a result, dialysis solution is drawn into the pump chamber 538A via the fluid pathways of the cassette 512.

This technique can be used to carry out a PD treatment in much the same way as described above with respect to the PD system 100. After treatment has been completed, the current applied to the electromagnets 535A, 535B in the piston heads 534A, 534B is reverse, causing a repelling force between the piston heads 534A, 534B and the membrane 540. This allows the user to easily remove the cassette 512 from the cassette compartment 114 with reduced risk of tearing the membrane 540.

While the piston heads 534A, 534B have been described as including electromagnets, permanently magnetic piston heads can alternatively or additionally be used. In such cases, permanent magnets, rather than electromagnets, can be contained in the cavities of the piston heads. In order to release the coupling between the permanently magnetic piston heads and the magnetically attractive membrane after treatment, the piston heads would be retracted a sufficient distance to overcome the magnetic coupling force.

While each of the piston heads 534A, 534B has been described as including a single magnet (electromagnet or permanent magnet), it should be understood that multiple magnets can be contained within the piston heads 534A, 534B to achieve a desired magnetic force.

While the membrane 540 has been described as including an outer layer of magnetically attractive material, such as paint or primer, in certain implementations, the magnetically attractive material is incorporated into the body of the membrane. For example, iron particles can be suspended within the body of the membrane.

While the membranes 140, 540 have been described as being attached only to the periphery of the base 156 of the cassettes 112, 512, in certain implementations the membranes 140, 540 are also attached (e.g., thermally or adhesively bonded) to the raised features 165A, 165B, 167 extending from the planar surface of the base 156.

While the membranes 140, 540 have been described as covering substantially the entire surface of the base 156 of the cassettes 112, 512, membranes covering only the pump chambers can alternatively be used. In such implementations, for example, the fluid pathways extending from the pump chambers of the cassette can be provided by tubing that is fluidly connected to the pump chambers.

While the cassettes discussed above have been described as having two pump chambers, the cassettes can alternatively have more or fewer than two pump chambers.

While each of the pump chambers of the cassettes described above has been described as including a fluid inlet port and a fluid outlet port, the pump chambers can alternatively include a single port that is used as both an inlet and an outlet.

While certain cassettes have been described as being positioned between locating pins and a lower ledge extending from a cassette interface of the PD cycler in order to hold the cassette in a position such that the actuator heads align with the pump chambers of the cassette, other techniques for ensuring that the actuator heads align with the pump chambers can alternatively or additionally be used. In some implementations, for example, the cassette is placed against the door of the PD cycler with the hollow projections of the cassette disposed in recesses of the PD cycler's door. The cassette is held in this position by retainer clips attached to the door. Upon closing the door, the actuator heads of the PD cycler align with the pump chambers of the cassette.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While the PD cyclers discussed above include inflatable pads in their doors to compress the cassette between the door and the cassette interface, the PD cyclers can alternatively or additionally include inflatable pads positioned behind the cassette interface. Similarly, as an alternative to or in addition to using an inflatable pad to compress the cassette, other mechanisms suitable for compressing the cassette can be used.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

Similarly, while the cassettes have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

What is claimed is:
1. A medical fluid pumping system, comprising:
 a medical fluid pumping machine defining a cassette enclosure, the medical fluid pumping machine comprising an actuator configured to reciprocate; and
 a medical fluid cassette configured to be disposed within the cassette enclosure of the medical fluid pumping machine, the medical fluid cassette comprising
 a base;

a membrane attached to the base, the membrane cooperating with a region of the base to define a fluid pump chamber and covering an entire area of the fluid pump chamber, the cassette positionable within the cassette enclosure of the medical fluid pumping machine so that the actuator is substantially aligned with the fluid pump chamber; and a member disposed within the fluid pump chamber, the member including a magnetically attractive material to couple the member to the actuator with a portion of the membrane positioned between the actuator and the member when the cassette is disposed within the cassette enclosure, wherein the member and the actuator are configured to be reciprocated together relative to the base when the member is coupled to the actuator.

2. The medical fluid pumping system of claim 1, wherein the member is shaped to substantially conform to a recess in the region of the base that cooperates with the membrane to form the fluid pump chamber.

3. The medical fluid pumping system of claim 2, wherein the member and the recess in the region of the base that cooperates with the membrane to form the fluid pump chamber are substantially dome-shaped.

4. The medical fluid pumping system of claim 1, wherein the actuator comprises one or more magnets, and the member comprises a magnetic material that is attracted to the magnets.

5. The medical fluid pumping system of claim 4, wherein the member comprises a magnetic plate that is secured to a non-magnetic material.

6. The medical fluid pumping system of claim 5, wherein the magnetic plate is surrounded by the non-magnetic material.

7. The medical fluid pumping system of claim 1, wherein the actuator comprises a magnet plate that defines a plurality of recesses and a plurality of magnets disposed in the recesses.

8. The medical fluid pumping system of claim 7, wherein the magnets are arranged in the recesses such that at least some adjacent magnets have opposite polarities.

9. The medical fluid pumping system of claim 8, wherein at least some of the magnets are arranged in a circular pattern, and all circumferentially adjacent magnets within the circular pattern have opposite polarities.

10. The medical fluid pumping system of claim 7, wherein the actuator further comprises a cover plate that can be secured to the magnet plate that defines the recesses to retain the magnets within the recesses.

11. The medical fluid pumping system of claim 1, wherein the member has a substantially flat surface that abuts a substantially flat surface of the actuator.

12. The medical fluid pumping system of claim 1, wherein the member is attached to the membrane of the cassette.

13. The medical fluid pumping system of claim 1, wherein the member comprises a first portion and a plurality of resilient legs extending from the first portion.

14. The medical fluid pumping system of claim 13, wherein the base defines channels configured to receive the legs to hold the member in a desired position within the chamber.

15. The medical fluid pumping system of claim 13, wherein the first portion is substantially dome-shaped.

16. The medical fluid pumping system of claim 1, wherein the actuator can be retracted a sufficient distance away from the base of the cassette to decouple the actuator from the member.

17. The medical fluid pumping system of claim 16, wherein the medical fluid pumping machine comprises a post that is arranged to be received in a bore at least partially formed by the actuator as the actuator is retracted, and the post can prevent movement of the member in a direction of the retracting actuator to facilitate decoupling of the actuator from the member.

18. The medical fluid pumping system of claim 1, wherein the medical fluid pumping machine comprises first and second actuators, and the membrane and regions of the base cooperate to define first and second fluid pump chambers, the cassette is positionable within the cassette enclosure of the medical fluid pumping machine so that the first and second actuators substantially align with the first and second fluid pump chambers, and first and second members are disposed within the first and second fluid pump chambers, respectively, the members being magnetically attracted to the actuators when the cassette is disposed within the cassette enclosure.

19. The medical fluid pumping system of claim 1, further comprising a cover that releasably attaches to the cassette, the cover comprising a projection that holds the member in contact with or in near contact with the base of the cassette when the cover is attached to the cassette.

20. The medical fluid pumping system of claim 1, wherein the medical fluid pumping system is a dialysis system.

* * * * *